US008754193B2

(12) United States Patent
Shusta et al.

(10) Patent No.: US 8,754,193 B2
(45) Date of Patent: Jun. 17, 2014

(54) GFABS: GFP-BASED BIOSENSORS POSSESSING THE BINDING PROPERTIES OF ANTIBODIES

(75) Inventors: Eric V. Shusta, Madison, WI (US); Tej Pavoor, Lebanon, NH (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/462,123

(22) Filed: May 2, 2012

(65) Prior Publication Data

US 2012/0277122 A1      Nov. 1, 2012

Related U.S. Application Data

(63) Continuation of application No. 12/589,764, filed on Oct. 28, 2009, now abandoned.

(60) Provisional application No. 61/197,858, filed on Oct. 31, 2008, provisional application No. 61/110,802, filed on Nov. 3, 2008.

(51) Int. Cl.
*C07K 17/00* (2006.01)
*C40B 40/00* (2006.01)

(52) U.S. Cl.
USPC ............................ 530/350; 530/802; 530/300

(58) Field of Classification Search
USPC .................................................. 530/350, 802
See application file for complete search history.

(56) References Cited

U.S. PATENT DOCUMENTS

| 6,638,732 | B1 * | 10/2003 | Evans ........................... 435/69.1 |
| 2006/0035289 | A1 | 2/2006 | Matsudaira et al. |
| 2010/0055728 | A1 | 3/2010 | Yang et al. |
| 2010/0196918 | A1 | 8/2010 | Ellis et al. |
| 2010/0261267 | A1 | 10/2010 | Waldo et al. |

OTHER PUBLICATIONS

Cetinkaya, et al., "How do insertions affect green fluorescent protein?", Chemical Physics Letters, 419:48-54 (2006).
Abedi, et al., "Green fluorescent protein as a scaffold for intracellular presentation of peptides", Nucleic Acids Research, 26(2):623-630 (1998).
Bajorath et al., Conformational Similarity and Systematic Displacement of Complementarity Determining Region Loops in High Resolution Antibody X-ray Structures, J. Bio. Chem., 1995, 270(38):22081-22084.
Chao et al., Isolating and Engineering Human Antibodies Using Yeast Surface Display, Nature Protocols, 2006, 1(2)155-768.
Chen et al., Selection of IgE-binding Aptameric Green Fluorescent Protein (Ap-GFP) by the Ribosome Display (RD) Platform, Biochem. Biophys. Res. Commun., 2008, 374:409-414.
Cormack et al., FACS-optimized Mutants of the Green Fluorescent Protein (GFP), Gene, 1996, 173:33-38.
Cormack et al., Yeast-enhanced Green Fluorescent Protein (yEGFP): A Reporter of Gene Expression in Candida Albicans, Microbiology, 1997, 143:303-311.
Crameri et al., Improved Green Fluorescent Protein by Molecular Evolution Using DNA Shuffling, Nature Biotechnology, 1996, 14:315-319.
Dai et al., Using T7 Phage Display to Select GFP-based Binders, Protein Engineering Design & Selection, 2008, 21:413-424.
Doi et al., Design of Generic Biosensors Based on Green Fluorescent Proteins with Allosteric Sites by Directed Evolution, FEBS Letters, 1999, 453:305-307.
Feldhaus et al., Flow-cytometric Isolation of Human Antibodies from a Nonimmune *Saccharomyces cerevisiae* Surface Display Library, Nature Biotechnology, 2003, 21:163-170.
Gilbreth et al., A Dominant Conformational Role for Amino Acid Diversity in Minimalist Protein—Protein Interfaces, J. Mol. Biol., 2008, 381:407-418.
Hackel et al., Picomolar Affinity Fibronectin Domains Engineered Utilizing Loop Length Diversity Recursive Mutagenesis, and Loop Shuffling, J. Mol. Biol., 2008, 381:1238-1252.
Hu et al., Simultaneous Visualization of Multiple Protein Interactions in Living Cells Using Multicolor Fluorescence Complementation Analysis, Nature Biotechnology, 2003, 21:539-545.
Huang et al., Secretion and Surface Display of Green Fluorescent Protein Using the Yeast *Saccharomyces cerevisiae*, Biotechnol. Prog., 2005, 21:349-357.
Huang et al., A Yeast Platform for the Production of Single-Chain Antibody-Green Fluorescent Protein Fusions, Appl. Env. Microbiol., 2006, 72(12):7748-7759.
Kiss et al., Antibody Binding Loop Insertions as Diversity Elements, Nuc. Acid Res., 2006, 34(19):e132.
Koide et al., High-affinity Single-domain Binding Proteins with a Binary-Code Interface, Proc. Natl. Acad. Sci. USA, 2007, 104:6632-6637.
Li et al., Identification of Sites Within a Monomeric Red Fluorescent Protein that Tolerate Peptide Insertion and Testing of Corresponding Circular Permutations, Photochem. Photobiol., 2008, 84:111-119.
Lipovsek et al., Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies, J. Mol. Biol., 2007, 368:1024-1041.
Miyawaki et al., Fluorescent Indicators for Ca2+ Based on Green Fluorescent Proteins and Calmodulin, Nature, 1997, 388:882-887.
Ormo et al., Crystal Structure of the Aequorea Victoria Green Fluorescent Protein, Science, 1996, 273:1392-1395.
Pavoor et al., Development of GFP-based Biosensors Possessing the Binding Properties of Antibodies, Proc. Natl. Acad. Sci. USA, 2009, 106(29):11895-11900.
Pedelacq et al., Engineering and Characterization of a Superfolder Green Fluorescent Protein, Nature Biotechnology, 2006, 24:79-88.
Peelle et al., Intracellular Protein Scaffold-Mediated Display of random Peptide Libraries for Phenotypic Svcreens in Mammalian Cells, Chemistry & Biology, 2001, 8:521-534.

(Continued)

*Primary Examiner* — Teresa Wessendorf
(74) *Attorney, Agent, or Firm* — Quarles & Brady, LLP

(57) ABSTRACT

A family of GFP scaffolds capable of accommodating two proximal, randomized binding loops is disclosed. GFP-based binders binding with nanomolar affinity are developed from a library of these GFP scaffolds.

7 Claims, 12 Drawing Sheets
(4 of 12 Drawing Sheet(s) Filed in Color)

(56) References Cited

OTHER PUBLICATIONS

Reid et al., Chromophore Formation in Green Fluorescent Protein, Biochem., 1997, 36:6786-6791.

Shaner et al., Improved Monomeric Red, Orange and Yellow Fluorescent Proteins Derived from *Discosoma* sp. Red Fluorescent Protein, Nature Biotechnology, 2004, 22:1567-1572.

Vogt et al., Construction of an Artificial Receptor Protein ("Anticalin") Based on the Human Apolipoprotein D, ChemBioChem., 2004, 5:191-199.

Waldo et al., Rapid Protein-Folding Assay Using Green Fluorescent Protein, Nature Biotechnology, 1999, 17:691-695.

Wang et al., Mining a Yeast Library for Brain Endothelial Cell-Binding Antibodies, Nature Methods, 2007, 4:143-145.

Zacharias et al., Partitioning of Lipid-Modified Monomeric GFPs Into Membrane Microdomains of Live Cells, Science, 2002, 296:913-916.

Zhang et al., Creating New Fluorescent Probes for Cell Biology, Nat. Rev. Mol. Cell Bio., 2002, 3:906-918.

Zhong et al., Enhanced Detection Sensitivity Using a Novel Solid-Phase Incorporated Affinity Fluorescent Protein Biosensor, Biomolecular Engineering, 2004, 21:67-72.

\* cited by examiner

| Protein | Denaturation Rate Constant (x 10³ min⁻¹) | Half-life Surface (min) | Half-life Soluble (min) |
|---|---|---|---|
| GFPM | 37 ± 1 | 19 | 12 |
| 20-1-6 | 410 ± 10 | 2 | ~ |
| 37-2-7 | 81 ± 2 | 9 | 7 |
| 70C-3 | 33 ± 1 | 21 | 17 |
| 20-4-8 | 38 ± 2 | 18 | ~ |
| 20-5-8 | 26 ± 2 | 26 | ~ |

Fig. 7
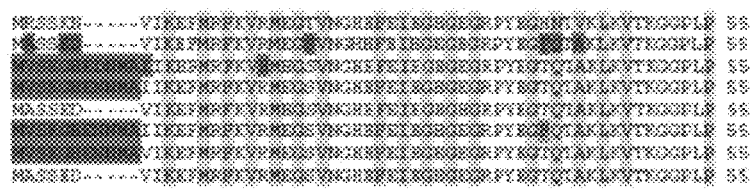
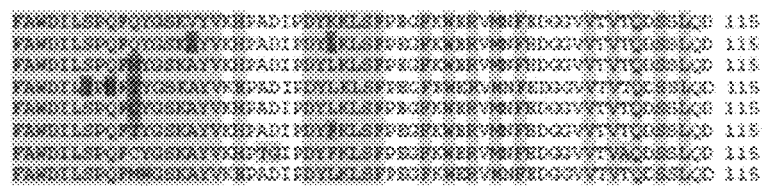
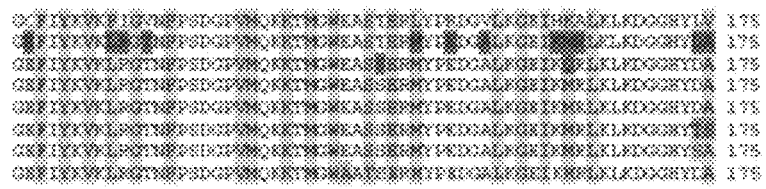
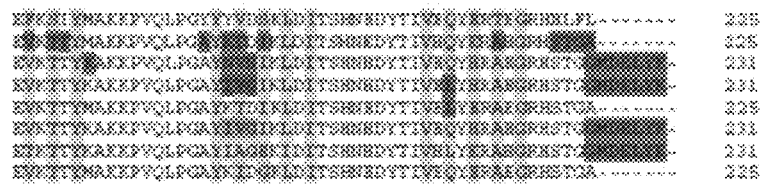

Fig. 12

DNA sequence of yEGFP
ATGTCTAAAG GTGAAGAATT ATTCACTGGT GTTGTCCCAA TTTTGGTTGA
ATTAGATGGT GATGTTAATG GTCACAAATT TTCTGTCTCC GGTGAAGGTG
AAGGTGATGC TACTTACGGT AAATTGACCT TAAAATTTAT TTGTACTACT
GGTAAATTGC CAGTTCCATG GCCAACCTTA GTCACTACTT TCGGTTATGG
TGTTCAATGT TTTGCGAGAT ACCCAGATCA TATGAAACAA CATGACTTTT
TCAAGTCTGC CATGCCAGAA GGTTATGTTC AAGAAAGAAC TATTTTTTTC
AAAGATGACG GTAACTACAA GACCAGAGCT GAAGTCAAGT TTGAAGGTGA
TACCTTAGTT AATAGAATCG AATTAAAAGG TATTGATTTT AAAGAAGATG
GTAACATTTT AGGTCACAAA TTGGAATACA ACTATAACTC TCACAATGTT
TACATCATGG CTGACAAACA AAAGAATGGT ATCAAAGTTA ACTTCAAAAT
TAGACACAAC ATTGAAGATG GTTCTGTTCA ATTAGCTGAC CATTATCAAC
AAAATACTCC AATTGGTGAT GGTCCAGTCT TGTTACCAGA CAACCATTAC
TTATCCACTC AATCTGCCTT ATCCAAAGAT CCAAACGAAA AGAGAGACCA
CATGGTCTTG TTAGAATTTG TTACTGCTGC TGGTATTACC CATGGTATGG
ATGAATTGTA CAAA Amino acid sequence of yEGFP
MSKGEELFTG VVPILVELDG DVNGHKFSVS GEGEGDATYG KLTLKFICTT
GKLPVPWPTL VTTFGYGVQC FARYPDHMKQ HDFFKSAMPE GYVQERTIFF
KD**DGNYKTRA EVKFEGDTLV NRIELKGIDF KEDGNILGHK
LEYNYNSHNV YIMADKQKNG IKVNFKIRHN IE**DGSVQLAD
HYQQNTPIGD GPVLLPDNHY LSTQSALSKD PNEKRDHMVL LEFVTAAGIT
HGMDELYKG

US 8,754,193 B2

GFABS: GFP-BASED BIOSENSORS POSSESSING THE BINDING PROPERTIES OF ANTIBODIES

CROSS-REFERENCE TO RELATED APPLICATION

This application is a continuation of U.S. application Ser. No. 12/589,764 filed Oct. 28, 2009, which claims priority from U.S. provisional patent application Ser. No. 61/197,858 filed Oct. 31, 2008, and Ser. No. 61/110,802 filed Nov. 3, 2008. All the above applications are incorporated by reference herein.

STATEMENT REGARDING FEDERALLY SPONSORED RESEARCH OR DEVELOPMENT

This invention was made with government support under EY018506 awarded by National Institute of Health. The government has certain rights in the invention.

BACKGROUND OF THE INVENTION

Antibodies have long been a mainstay of biological and medical research, and current use of antibodies as therapeutics has further expanded their portfolio of applications. More recently, to address various challenges such as the reduced stability and production yields of the antibody fragments that are frequently employed in in vitro evolution platforms, and in large part as a result of intellectual property concerns, the field of alternative binding scaffolds has emerged (Skerra A., *Curr. Opin. Biotechnol.*, 18:295-304, 2007). By mutagenizing solvent-exposed loop regions or inserting diverse loop repertoires into non-antibody protein scaffolds, specific binding attributes can be conferred to proteins that naturally have desirable properties such as high stability and production titers. In this way, alternative scaffolds such as the 10th human fibronectin type III domain (Lipovsek D et al., *Journal of Molecular Biology*, 368:1024-1041, 2007), anticalins (Korndorfer I P et al., *Journal of Molecular Biology*, 330:385-396, 2003; Schlehuber S et al., *Journal of Molecular Biology*, 297:1105-1120, 2000; Vogt M & Skerra A, *Chembiochem* 5:191-199, 2004), designed ankyrin repeat proteins (Zahnd C et al., *Journal of Molecular Biology*, 369:1015-1028, 2007), and Affibodies (Nord K et al., *Eur J Biochem*, 268:4269-4277, 2001; Nord K et al., *Nat Biotechnol*, 15:772-777, 1997), among others, have been developed to bind to targets with antibody-like affinity.

Green fluorescent protein (GFP) has also been explored as a potential alternative scaffold. To date, GFP has been utilized for a wide variety of different applications (Zhang J et al., *Nat Rev Mol Cell Biol*, 3:906-918, 2002) including $Ca^{2+}$ detection (Miyawaki A et al., *Nature*, 388:882-887, 1997), visualization of protein-protein interactions (Hu C D & Kerppola T K, *Nature Biotechnology*, 21:539-545, 2003), and as a reporter for protein folding (Waldo G S et al., *Nature Biotechnology*, 17:691-695, 1999). Considerable effort has also been expended in attempts to develop GFP as a binding scaffold that would have two potential advantages over the aforementioned alternative scaffolds. First, by combining binding attributes with the intrinsic fluorescence of the GFP protein, the proteins could act as single step detection reagents in applications such as fluorescence-based ELISAs, flow cytometry, and intracellular targeting/trafficking in live cells. Second, GFP fluorescence requires that the protein is properly folded (Reid B G & Flynn G C, *Biochemistry*, 36:6786-6791, 1997) offering an in situ metric for folding fidelity, absent from other alternative scaffolds. Such a folding probe could assist both assessment of library fitness upon binding loop introduction, and subsequent selection of properly-folded, soluble clones.

Several attempts have been made to confer binding capability to GFP by inserting binding loops into various solvent-exposed turns that connect the β-strands of the GFP β-barrel structure. The regions of GFP that are most amenable to insertion of amino acids have been determined (turns Gln157-Lys158 and Glu172-Asp173) (Abedi M R et al., *Nucleic Acids Research*, 26:623-630, 1998; Doi N & Yanagawa H, *Febs Letters*, 453:305-307, 1999), although fluorescence is diminished substantially, and when random loops were inserted, the resultant library fluorescence decreased to 2.5% of wild-type (Abedi M R et al., *Nucleic Acids Research*, 26:623-630, 1998). Selection of GFP-inserted peptide libraries for targeting various intracellular compartments has also been performed (Peelle B et al., *Chem Biol*, 8:521-534, 2001).

GFP-inserted peptide libraries have also been selected to identify peptides useful for targeting various intracellular compartment. Antibody heavy chain CDR3 sequences have been inserted into several loop regions of superfolder GFP, a GFP variant evolved for high stability and improved folding kinetics (Pedelacq J D et al., *Nature Biotechnology*, 24:79-88, 2006), to create libraries of single CDR3-inserted GFP. Results from this study indicated that insertion at many sites substantially reduces GFP fluorescence as seen previously with standard GFP variants (Kiss C et al., *Nucleic Acids Research*, 34:15, 2006). Three loop regions of the superfolder GFP, however, tolerated single loop CDR insertions (including Asp173-Gly174) such that it was possible to isolate fluorescent binders against protein targets using T7 phage display, with the best being a 470 nM lysozyme binder (Dai M et al., *Protein Engineering Design & Selection*, 21:413-424, 2008). This level of affinity is in the realm of that found for peptide binders (Craig L et al., *J Mol Biol*, 281:183-201, 1998) likely as a consequence of its single binding loop design. Affinity of GFP-based binding proteins could therefore in principle benefit from display of multiple binding loops which could act together to form a cooperative binding interface. However, the lone examples of multiple loop insertion into GFP include insertion of haemagglutinin peptide (Zhong J Q et al., *Biomolecular Engineering*, 21:67-72, 2004) or random loops (Chen S-S et al., *Biochem. Biophys. Res. Commun.*, p. doi:10.1016/j.bbrc.2008, 2008).1006.1123 into two loops on opposite faces of GFP. While suitable for the authors' goals, these insertion locations would not be ideal for forming a cooperative binding interface. Moreover, GFP fluorescence of the resulting clones in the case of the random loop libraries was not demonstrated (Chen S-S et al., *Biochem. Biophys. Res. Commun.*, p. doi:10.1016/j.bbrc.2008, 2008).

Thus, to date, robust fluorescent multiple loop-inserted GFP repertoires have not been described, even using the superfolder GFP as a template.

SUMMARY OF THE INVENTION

In this study, the GFP scaffold itself was evolved to maintain its fluorescence properties in the presence of two inserted binding loops, and we demonstrated that scaffolds designed in this way are capable of accepting a diverse loop repertoire from which fluorescent binding proteins could be isolated.

In one embodiment, the present invention is a fluorescent biosensor comprising a fluorescent protein scaffold with heterologous amino acid sequence insertions between Glu172 and Asp173 and between Asp102 and Asp103, wherein the scaffold has the mutations D19N, F64L, and A87T and wherein the protein is selected from the group of GFP and GFP variants. In another embodiment, the biosensor additionally comprises the mutation V163A. In yet another embodiment, the biosensor additionally comprises the mutations Y39H, N105T, D117G, E172K and L221V. In yet another embodiment, the biosensor additionally comprises the mutation F223S. Preferably, the protein scaffold is GFP.

In one embodiment, the fluorescence per molecule of the biosensor is at least 10% that of a non-loop inserted GFP. Preferably, the fluorescence per molecule of the biosensor is at least 20% that of a non-loop inserted GFP. More preferably, the fluorescence per molecule of the biosensor is at least 40% that of a non-loop inserted GFP.

In one embodiment, the invention is a fluorescent biosensor comprising a green fluorescent protein scaffold, or a GFP variant protein scaffold, with heterologous amino acid sequence insertions between Glu172 and Asp173, and between Asp102 and Asp103, wherein the scaffold has the mutations D19N, F64L, A87T, V163A and Y39H. In one embodiment, the heterologous amino acid sequence insertion between Glu172 and Asp173 is selected from the group consisting of SEQ ID NO: 30 and SEQ ID NO: 34, and the heterologous amino acid sequence insertion between Asp102 and Asp103 is selected from the group consisting of SEQ ID NO: 29 and SEQ ID NO: 33, and the biosensor is capable of specifically binding TrkB.

In another embodiment, the invention is a fluorescent biosensor comprising a green fluorescent protein scaffold, or a GFP variant protein scaffold, with heterologous amino acid sequence insertions between Glu172 and Asp173, and between Asp102 and Asp103, wherein the scaffold has the mutations D19N, F64L, A87T, V163A, Y39H, N105T, D117G, E172K and L221V. In one embodiment, the heterologous amino acid sequence insertion between Glu172 and Asp173 is according to SEQ ID NO: 32, and heterologous amino acid sequence insertion between Asp102 and Asp103 is according to SEQ ID NO: 31, and the biosensor is capable of specifically binding TrkB. In another embodiment, the heterologous amino acid sequence insertion between Glu172 and Asp173 is selected from the group consisting of SEQ ID NOs: 36, 38, 40 and 42, and heterologous amino acid sequence insertion between Asp102 and Asp103 is selected from the group consisting of SEQ ID NOs: 35, 37, 39 and 41, and the biosensor is capable of specifically binding GAPDH.

In one embodiment, the present invention is an expression library comprising multiple fluorescent biosensors, wherein the fluorescent biosensor comprises a green fluorescent protein scaffold, or a GFP variant protein scaffold, with heterologous amino acid sequence insertions between Glu172 and Asp173, and between Asp102 and Asp103, wherein the scaffold has the mutations D19N, F64L, and A87T and wherein the heterologous amino acid sequence insertions are not identical. In another embodiment, the biosensor additionally comprises the mutation V163A. In yet another embodiment, the biosensor additionally comprises the mutations Y39H, N105T, D117G, E172K and L221V.

In one embodiment, the present invention is an expression library comprising at least two fluorescent protein scaffolds, wherein the fluorescent protein scaffolds are not identical.

In one embodiment, the present invention is a method of detecting an antigen comprising exposing a biosensor to a specific antigen and detecting binding via fluorescence. In one embodiment, the biosensor is a fluorescent biosensor comprising a fluorescent protein scaffold with heterologous amino acid sequence insertions between Glu172 and Asp173, and between Asp102 and Asp103, wherein the scaffold has the mutations D19N, F64L, and A87T and wherein the protein is selected from the group of GFP and GFP variants. In another embodiment, the biosensor additionally comprises the mutation V163A. In yet another embodiment, the biosensor additionally comprises the mutations Y39H, N105T, D117G, E172K and L221V.

In another embodiment, the present invention is a method of isolating a peptide sequence that will bind to a target molecule comprising exposing the target molecule to an expression library described above and determining which library members bind to the target molecule.

In another embodiment, the present invention is a fluorescent biosensor comprising a fluorescent protein scaffold with heterologous amino acid sequence insertions, wherein the scaffold has mutations corresponding to D19N, F64L and A87T, wherein the protein is selected from the group consisting of GFP and GFP variants. Preferably, the heterologous amino acid sequence insertions are located within any of the ten solvent-accessible loops.

In another embodiment, the present invention is an expression library comprising fluorescent biosensors, wherein the fluorescent biosensors comprise a fluorescent protein scaffold with heterologous amino acid sequence insertions, wherein the heterologous amino acid sequence insertions are not identical, wherein the scaffold has mutations corresponding to D19N, F64L and A87T and wherein the protein is selected from the group consisting of GFP and GFP variants.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 is a sequence comparison of preferred various fluorescent proteins suitable for the present invention. The figure indicates sequences as well as the point mutations that yield six variants of red fluorescent protein. (Taken from Shaner, N. et al., Improved monomeric red, orange and yellow fluorescent protein derived from *Discosoma* sp. red fluorescent protein, *Nature Biotechnol.*, 22:1567-1572, 2004.)

FIG. 12 is the nucleic acid and amino acid sequence of yeast codon optimized GFP. "**" indicates location of insertion. The first location is between D102 and D103, and the second location is between E172 and D173.

DESCRIPTION OF THE INVENTION

In General

Figure 1:
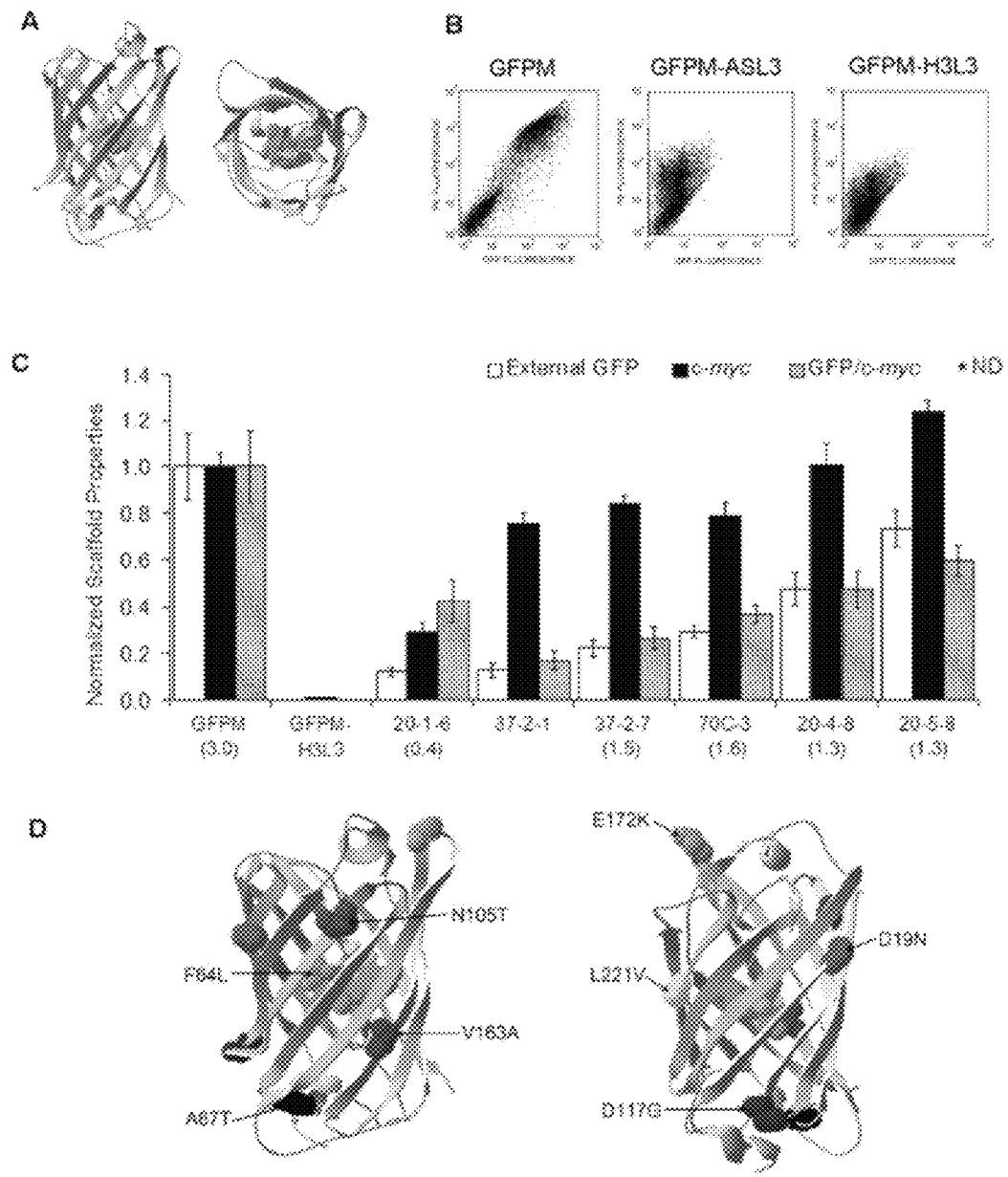
FIG. 1 discloses directed evolution of a set of dual loop-compatible scaffolds. Panel A shows side view and top view of GFPM with loop insertion site Asp102-Asp103 highlighted in red and Glu172-Asp 173 highlighted in blue. The chromophore residues are shown in space-fill green. The structure used was that of GFP with the S65T mutation pdb ID=1EMA (Ormo M et al., *Science*, 273:1392-1395, 1996). Panel B shows flow cytometric dot plots for surface displayed GFPM, single loop-inserted GFPM-ASL3, and dual loop-inserted GFPM-H3L3. PE fluorescence (y-axis) is indicative of full length expression using the c-terminal c-myc epitope for detection and GFP fluorescence (x-axis) is indicative of properly folded GFPM or its variants. The negative population lacking both PE and GFP fluorescence located in the lower left quadrant of dot plots in panel B is a non-displaying population characteristic of yeast display. In panel C, fluorescence (external GFP), full-length expression (c-myc), and fluorescence per molecule (GFP/c-myc) for the evolved scaffolds were normalized to non loop-inserted GFPM for comparison. All data were derived using flow cytometry of triplicate yeast transformants induced for display at 20° C. It is important to note the GFP fluorescence measured via flow cytometry comprises an internal contribution from protein retained inside the cell as well as an external contribution from the displayed protein. Only the external contribution to the fluorescence is reported here (see Supplemental methods for details). Clones are named based on the selection from which they were recovered, except for 20-5-8 which was recovered in both the 20° C. and 37° C. selections. ND denotes the absence of a detectable signal. Secretion yields for the various scaffolds using a baseline expression system are denoted beneath each scaffold in (mg/L). Panel D shows GFPM structure with residues mutated in the 20-5-8 scaffold highlighted. Loop insertion site Asp102-Asp103 is highlighted in red and Glu172-Asp173 is highlighted in blue. Structure on right was generated by rotating the structure on the left 180° to allow a clearer view of several of the mutations.

To take advantage of any potential benefits afforded by multiple binding loops, we undertook to evolve the a fluorescent protein scaffold, preferably GFP, to maintain its fluorescence properties under conditions of dual loop insertion. Our goal was to provide a biosensor with both specificity and detection capabilities, so it is important that the evolved scaffold be suitable for forming a cooperative binding interface.

By "scaffold," we mean the fluorescent protein that will serve as a backbone of the "inserted binding loops" or "surrogate loops." We refer to the combination of the scaffold and the binding loops as the "biosensor" or the "FPAb". If the biosensor comprises a GFP scaffold, we refer to it as a "GFAb."

Our approach contrasts significantly from all previous studies where binding loops were simply inserted into pre-existing GFP variants. Even though some of these previously created molecules had at least minimal florescence and, in the case of superfolder GFP, were stable, the molecules are neither optimized for nor amenable to multiple binding loop insertion. To this end, we employed a "surrogate loop" approach to evolve GFP to withstand insertion of amino acids at two proximal loop locations and thereby form a putative binding surface. By "surrogate loop" or "inserted binding loop," we mean a section of heterologous sequence inserted at two specific GFP locations: Glu172-Asp 173 and Asp102-Asp103. Although Glu172-Asp 173 and Asp102-Asp103 were chosen as preferable insertion sites in the working examples described below, one could also use other locations as insertion sites in other embodiments of the invention, as long as the locations fall into any of the ten solvent-accessible loops (Abedi, M. R., et al., *Nulceic Acids Res.*, 26:623-630, 1998; Ormo, M., et al., *Science*, 273:1392-1395, 1996).

Biosensors of the Present Invention

Pavoor, et al. (2009, *Proc. Natl. Acad. Sci. U.S.A.*, 106(29): 11895-11900, E-publication, incorporated by reference) is an academic manuscript authored by the inventors and describes one embodiment of the present invention.

In one embodiment, the present invention is an optimized fluorescent scaffold capable of dual surrogate loop insertion. In a preferred version of the present invention, the scaffold is based on GFP sequence, preferably yEGFP sequence (see SEQ ID NO:1 for DNA sequence and SEQ ID NO:2 for amino acid sequence). The surrogate loops, preferably comprising 12 and 13 amino acids of heterologous peptide sequence respectively although one could substitute other peptide lengths, will be inserted at Glu172-Asp 173 and Asp102-Asp103. Loop-length diversity is well known at these sites (Koide, A., et al., *Gene*, 173:33-38, 1996; Hackel, B. J., et al., *J. Mol. Biol.*, 381:1238-1252, 2008).

In another preferred version of the present invention the scaffold is based on "GFP variants." By "GFP variant", we mean a fluorescent protein comprising a sequence that is substantially identical (95% or preferably at least 99% amino acid sequence homolog) to GFP with mutations that have altered the fluorescence profile. Table 1 below presents particularly desirable GFP variants. The protein sequences of the GFP variants in Table 1 vary from between 1 amino acid change relative to GFP (YFP, BFP, CFP) and 9 amino acid changes relative to GFP (radiometric phluorin). A most preferred variant has 1-3 amino acid changes. A preferred variant has less than 10 changes.

The present invention is also suitable for non-GFP fluorescent proteins. For example, Table 2 lists another group of preferred FPs that are not based on GFP sequence. To use these proteins in the present invention, one would make mutations corresponding to the successful mutations in GFP described below. FIG. 7 is a sequence comparison of preferred various FPs suitable for the present invention.

One would mutagenize the FPs in Table 2 at the corresponding mutations: E19N, E39H, F65L, S86T, N103T, and M164A. Gly117 will remain as it is in wild-type red fluorescent proteins. One would insert one loop between Ala183 and Lys 184 since this has been shown to be amenable to insertion in a previous study (Li, Y., *Photochem. Photobiol.*, 84:111-119, 2008). The other loop would be Arg153 and Asp154.

TABLE 1

| GFP variants | |
|---|---|
| Yellow Fluorescent Protein (YFP) | YFP has the mutation T203Y (Wachter, R., et al, Structure Fold. Des., 6, 1267-1277 (1998)) Citrine and Venus are variants of YFP |
| Blue Fluorescent Protein (BFP) | BFP has the mutation Y66H (Yang, T., et al, J. Biol. Chem., 273, 8212-8216 (1998)) |
| Enhanced Blue Fluorescent Protein (EBFP) | EBFP is brighter than BFP and has the mutations Y66H, F64L, S65T, and Y145F (Yang, T., et al, J. Biol. Chem., 273, 8212-8216 (1998)) |
| Cyan Fluorescent Protein (CFP) | CFP has the mutation Y66W (Hein, R., et al, Current Biology, 6, 178-182 (1996)) |
| Enhanced Cyan Fluorescent Protein (ECFP) | ECFP has the mutations Y66W, N146I, M153T, V163A, N212K (Hein, R., et al, Current Biology, 6, 178-182 (1996)) Cerulean: ECFP + S72A Y145A H148D CytoGem ™ Emerald-Green (S65T/S72A/N149K/M153T/I167T/H231L) CytoGem ™ Topaz-Gold (S65G/S72A/K79R/T203Y/H231L) Sapphire fluorescent protein |
| Photoactivable GFP (PA-GFP) | PA-GFP is not fluorescent till it is exposed to light of a specific wavelength (PA-GFP) has the mutation T203H (Shaner, N. et al, Journal of Cell Science, 120, 4247-4260 (2007)) |
| pH Sensitive GFPs | (Miesenbock, G. et al, Nature, 394, 192-195 (1998)) Ratiometric pHluorin has the mutations S202H, E132D, S147E, N149L, N164I, K166Q, I167V, R168H, and L220F. Ecliptic pHluorin has the mutations S147D, N149Q, T161I, S202F, Q204T, and A206T. |

TABLE 2

Other FPs

| | |
|---|---|
| Red Fluorescent Proteins | Red fluorescent protein and its variants as documented in Shaner, N et al, Nature Biotechnology, 24, 1567-1572, 2004 incorporated by reference. |

In one embodiment of the invention, the GFP or GFP variant scaffold comprises the three mutations found to be necessary for all suitable clones: D19N, F64L, and A87T. In one preferred embodiment, the scaffold has the additional mutation described in clone 37-2-7, V163A. In a preferred embodiment, this scaffold has the mutations of 37-2-7 with the additional mutations disclosed in clone 20-5-8, which are Y39H, N105T, D117G, E172K and L221V. In another version of the present invention, the scaffold has the mutations of 20-5-8 with the additional mutation described in D20-5-1, F223S.

The scaffolds of the present invention are suitable to form biosensors, wherein surrogate loops are inserted at scaffold positions 172/173 and 102/103 and are typically 12 and 13 amino acids, respectively. The surrogate loops may comprise any heterologous amino acid sequence and are preferably adapted to bind to a target. By "heterologous amino acid sequence", we mean an amino acid sequence that is not part of the native GFP sequence. By "target" we mean peptides, small molecules, nucleic acids and other molecules with antigenic characteristics.

Figure 10:
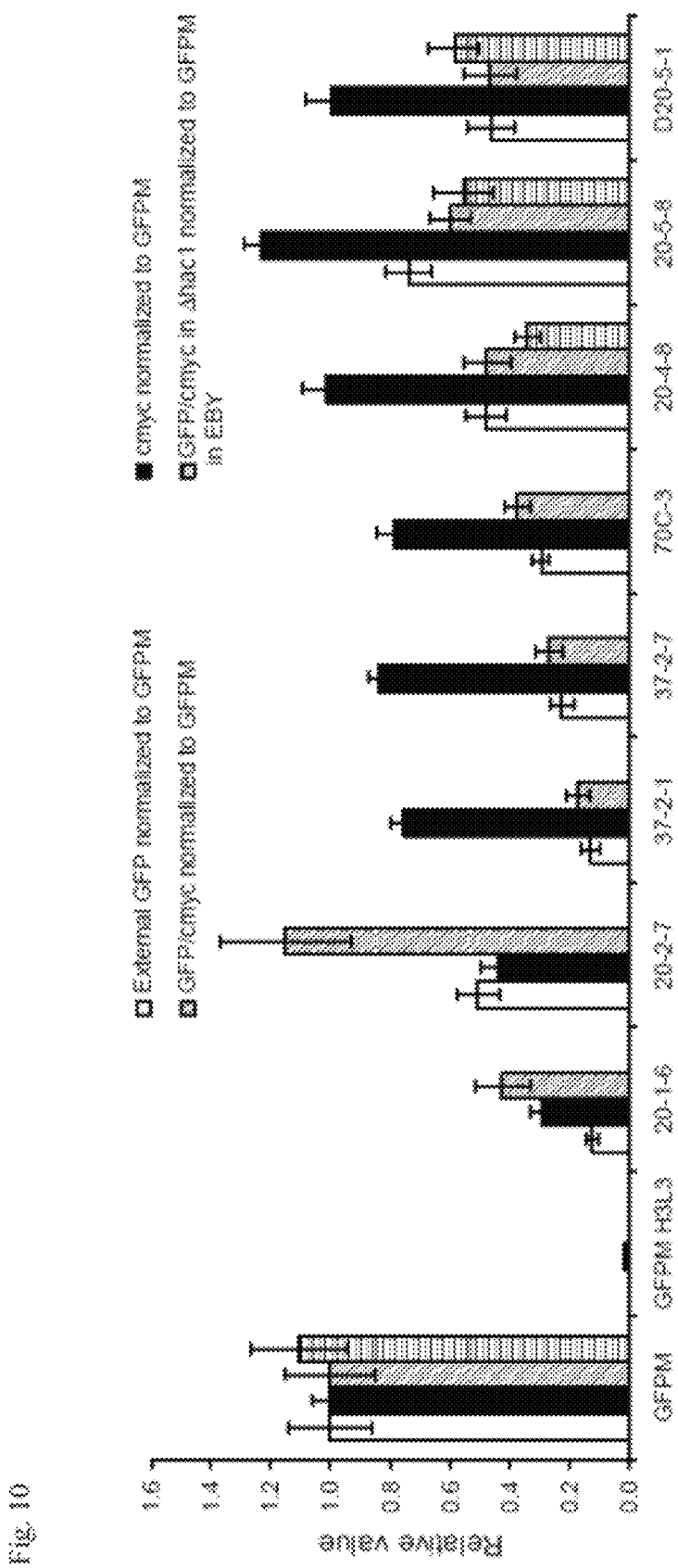
FIG. 10 is a bar graph disclosing properties of the scaffolds on the surface of yeast using various protein engineering strategies. This represents quantification of properties of the scaffold expressed on the surface of yeast. All yeast cells were induced at 20° C. and the properties of the scaffold on the surface of yeast were analyzed using a flow cytometer. Each data point represents triplicate samples. The surrogate binding loop inserted GFP lacked fluorescence and expression (GFPM H3L3). There was an improvement in both fluorescence and expression after each round of protein engineering. The external fluorescence per molecule of the scaffold on the surface of yeast also increased progressively. The external fluorescence per molecule for GFPM was higher when expressed in Δhac1 cells indicating that GFPM was unaffected by the lack of the UPR in Δhac1. However, the external fluorescence per molecule was lower for 20-4-8 forming the basis of the selection screen utilized for Δhac1. Both 20-5-8 and D20-5-1 evolved using Δhac1 cells were found to have an external fluorescence per molecule higher that 20-4-8 indicating their ability to overcome any deficiency in processing in UPR deficient cells.

Biosensors of the present invention will maintain suitable "brightness" after the insertion of the two surrogate loops into the scaffold structure. FIGS. 1C and 10 illustrate suitable brightness. By "brightness", we mean fluorescence per molecule of the biosensor. A biosensor of the present invention has at least the brightness of clone 20-1-6, at least 10% that of the non-loop inserted GPF control. Preferably, the brightness is at least 70% the fluorescence of GFP on the surface of yeast. FIGS. 1C and 10 also present preferable brightness profiles of at least 20% the brightness of GFP and at least 40% the brightness of GFP.

One may create scaffolds and biosensors of the present invention by commonly understood biochemical and molecular biological methods. Preferred methods are disclosed in the Examples and below.

In another embodiment, the present invention is an expression library of biosensors. By "expression library", we mean a population of organisms, each of which carries a DNA molecule expressing a distinct protein. For example, the Examples disclose yeast display libraries and methods of creating these libraries to express or display biosensors of the present invention. However, one of skill in the art may wish to use other types of expression libraries, such as phage display, ribosome display and bacteria display. The Examples disclose advantages and disadvantages to the yeast display system. Because the standard yeast display system has advantages such as the ability to rapidly quantify and compare protein properties such as stability and binding affinity directly on the surface of the yeast, yeast display is especially suited for engineering fluorescent proteins. However, other systems may be suitable for other applications. For example, the Examples disclose that bacterial approaches to engineering GFP routinely employ improvements in intracellular fluorescence as the main readout for correct folding, solubility and fluorescence.

In a preferred embodiment, the expression library would comprise at least two fluorescent protein scaffolds, wherein the fluorescent protein scaffolds are not identical.

Preferably, an expression library of the present invention will comprise at least $10^6$ clones. Most preferably, the library will comprise at least $10^8$ clones.

Use of Biosensors of the Present Invention

Biosensors of the present invention are suitable for detection of any desired antigen target or binding target of interest.

In one preferred method of the present invention, one would expose a biosensor library to an antigen or target of interest and determine which clone within the library has suitable binding characteristics. In this manner, one could determine which binding loops are capable of binding to the target of interest and could isolate or investigate specific peptides that have desirable binding characteristics.

In another method of the present invention, one may be interested in constructing a biosensor with surrogate loops with known binding properties against a target molecule and using that biosensor to detect the molecule in test samples.

In general, we envision the following applications for FPAbs:

GFAbs and FPAbs can be utilized in molecular detection assays such as Western blots, Enzyme Linked Immunosorbent Assays (ELISAs), flow cytometry, immunocytochemistry, immunohistochemistry, and immunoprecipitation. In essence, GFAbs and FPAbs offer an inexpensive alternative to antibodies with the advantage of allowing for one step detection of the binding event due to their intrinsic fluorescence. Further, GFAbs and FPAbs can also be used for real time monitoring of protein localization and trafficking inside cells as well as to study protein-protein interactions via fluorescence resonance energy transfer (FRET) between GFAbs and FPAbs modified to emit at different wavelengths.

One can opt to use expression libraries described herein to isolate GFAbs and FPAbs against a variety of different proteins and small molecules commonly utilized in research and diagnostic applications. Such an establishment can also offer tailor-made services to isolate GFAbs and FPAbs against newly discovered proteins or molecules. For example, a research group may identify a protein inside the cell that is important in the onset of Parkinson's disease. Instead of raising antibodies against the protein by immunization of animals, the present invention offers an inexpensive one-step detection alternative. Briefly, the libraries described herein can be screened to isolate a GFAb or FPAb that binds the protein with high affinity. This GFAb or FPAb can then be produced in a large amount using yeast. The GFAb or FPAb binds the protein and allows its detection via fluorescence of the GFAb or FPAb. This GFAb or FPAb can be utilized to perform ELISAs, flow cytometric experiments, and allows for real time trafficking of the protein inside the cell.

The present invention has been described above with respect to its preferred embodiments. Other forms of this concept are also intended to be within the scope of the claims.

EXAMPLES

Proteins that can bind specifically to targets that also have an intrinsic property allowing for easy detection could facilitate a multitude of applications. While the widely used green fluorescent protein (GFP) allows for easy detection, attempts to insert multiple binding loops into GFP to impart affinity for a specific target have been met with limited success due to the structural sensitivity of the GFP chromophore. In this study, directed evolution using a surrogate loop approach and yeast surface display yielded a family of GFP scaffolds capable of accommodating two proximal, randomized binding loops. The library of potential GFP-based binders or GFAbs was subsequently mined for GFAbs capable of binding to protein targets. Identified GFAbs bound with nanomolar affinity and required binding contributions from both loops indicating the advantage of a dual loop GFAb platform. Finally, GFAbs were solubly produced and used as fluorescence detection reagents to demonstrate their utility.

Effects of Single and Dual Loop Insertions on GFP Expression and Fluorescence

The initial goal of this study was to evaluate the capability of monomeric yeast enhanced green fluorescent protein (GFPM) (Cormack B P et al., *Microbiology-Uk,* 143:303-311, 1997; Zacharias D A et al., *Science,* 296:913-916, 2002) (see Materials and Methods for details) to accommodate dual loop insertions. The Glu172-Asp173 turn region was chosen as one insertion site since earlier studies have shown that GFP can retain its fluorescence upon insertions of various lengths at this location (Abedi M R et al., *Nucleic Acids Research,* 26:623-630, 1998; Doi N & Yanagawa H, *Febs Letters,* 453: 305-307, 1999) (FIG. 1A). The second location selected was turn Asp102-Asp103 due to its proximity (about 1.6 nm) to Glu172-Asp173 on the same face of the β-barrel allowing the eventual possibility of improved affinity for targets through cooperative antigen binding with both inserted loop regions (FIG. 1A).

Figure 8:
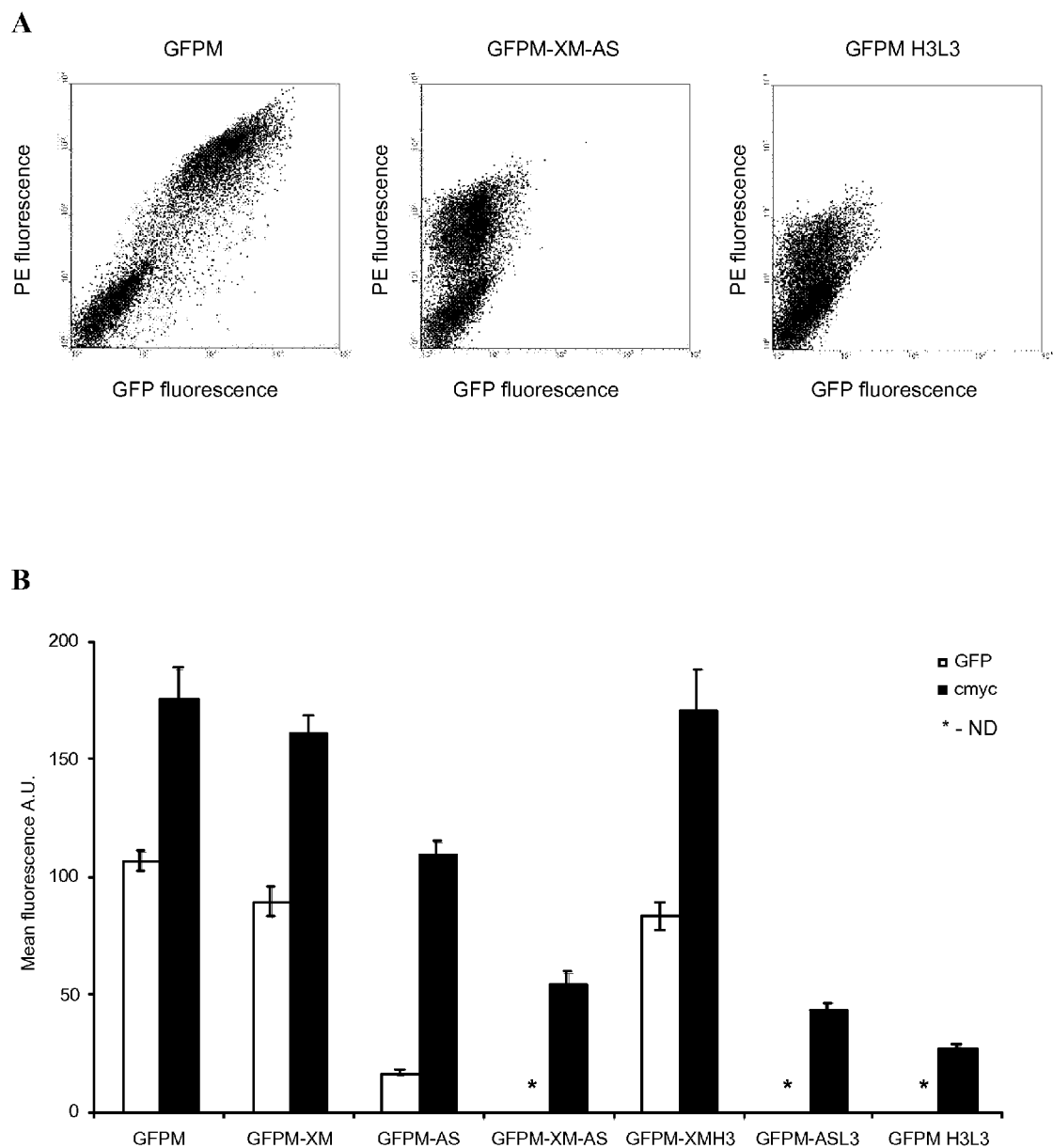
FIG. 8 shows effect of inserting restriction sites on the fluorescence and expression of GFPM on the surface of yeast. Panel A is dot plots of GFPM, dual restriction site dual loop insertion GFPM-XM-AS, and dual surrogate binding loop insertion GFPMH3L3. The Y axis indicates full length expression and the X axis is a read out for fluorescence. Both fluorescence and expression were reduced with insertion of restriction sites as well as longer surrogate binding loops in the two selected loop regions of GFPM. Panel B shows effect of insertions in two different regions of GFPM determined by measuring inherent GFP fluorescence as well as expression on the surface of yeast. All yeast samples were labeled with anti c-myc and anti-mouse phycoerythrin antibodies. Expression was induced at 20° C. and the data shown is average of triplicate samples. ND denotes the absence of a detectable signal.

Restriction sites (four amino acids each) were inserted into the two loop regions of GFP to allow for subcloning of loops into the two locations (FIG. 1A). The resulting proteins were analyzed via yeast surface display. As expected, the insertion of the four amino acids into loop Glu172-Asp173 (GFPM-XM) allowed unaltered surface expression and GFP fluorescence (FIG. 8). In contrast, the insertion of four amino acids at Asp102-Asp103 significantly reduced both GFP fluorescence and surface expression levels (GFPM-AS) (FIG. 8). The insertion of restriction sites at both loop positions (GFPM-AS-XM) resulted in a non-fluorescent protein with markedly reduced expression on the surface of yeast.

Figure 4:
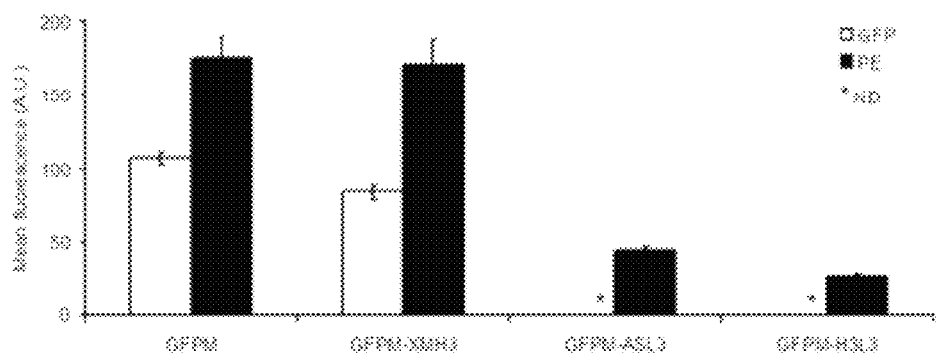
FIG. 4 discloses properties of dual surrogate loop-inserted GFPM. Quantitative expression (PE) and fluorescence (GFP) flow cytometric data are presented as the mean±SD of triplicate independent yeast transformants. ND denotes the absence of a detectable signal.

Surrogate binding loops in the form of CDRH3 and CDRL3 from the D1.3 anti-lysozyme antibody (Bajorath J et al., *Journal of Biological Chemistry,* 270:22081-22084, 1995) were inserted into positions Glu172-Asp173 and Asp102-Asp103, respectively (Tables 7 and 8), and the resultant constructs were displayed on the surface of yeast. While a single loop inserted at the Glu172-Asp173 site of GFPM (GFPM-XMH3) could retain GFP fluorescence and expression on the surface of yeast as expected (FIGS. 4 and 8), single loop insertion at Asp102-Asp103 (GFPM-ASL3) ablated all GFP fluorescence and much of the surface expression (FIG. 1B and FIG. 4). When both loops were inserted (GFPM-H3L3), very little surface display was detected and the protein possessed no fluorescence (FIGS. 1B, 4 and 8).

Figure 6:
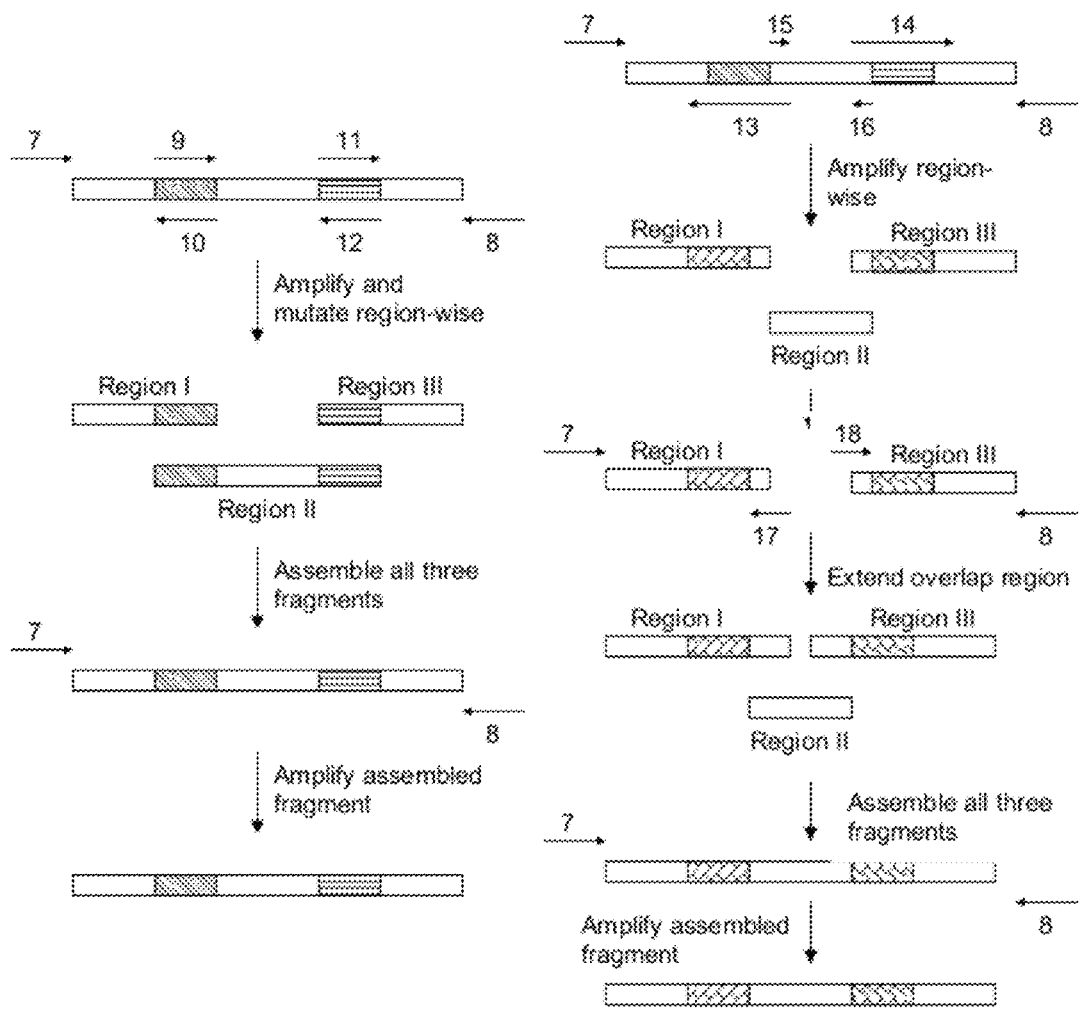
FIG. 6 is a schematic of our strategy to create library of GFP scaffolds (left) and random loop libraries (right). Primer numbering matches description in Table 7.
Figure 9:
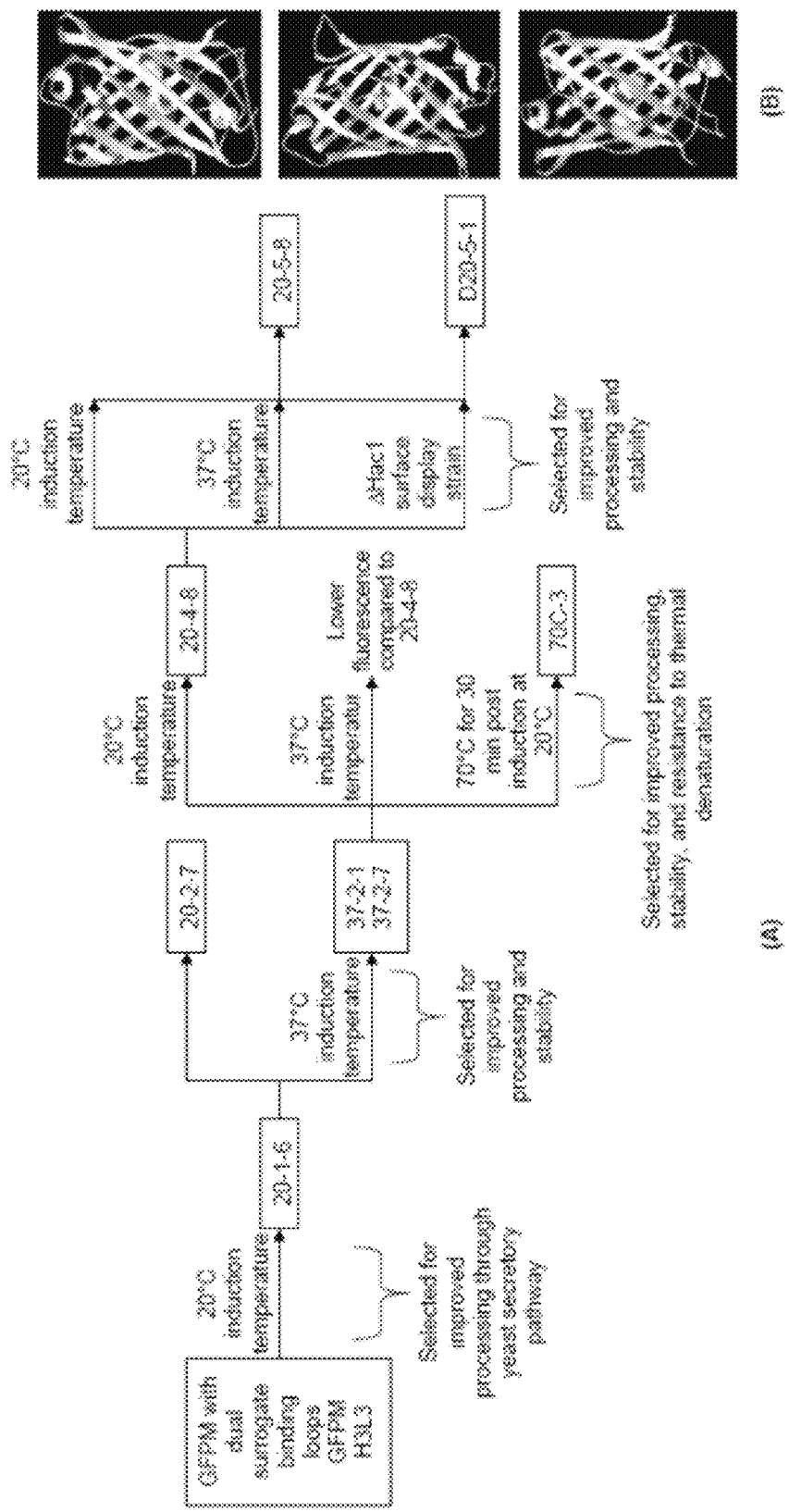
FIG. 9 is a protein engineering scheme followed in this study and a ribbon representation of GFP indicating positions of mutations. In panel A, starting with GFPM H3L3, which was not fluorescent and not expressed on the surface of yeast, the scaffold was mutated and the library sorted by utilizing induction at 20° C. as a screen. The best clone 20-1-6 was further mutated and sorted at two induction temperatures: 20° C. and an elevated induction temperature of 37° C. to isolate more stable scaffolds. 37-2-1 and 37-2-7 evolved from the elevated induction temperature strategy were mutated and the library was sorted again at the two induction temperatures to yield 20-4-8 which had the highest fluorescence and expression among the scaffolds isolated from that sort round. 20-4-8 was used as the template for mutagenesis and the library was sorted at the two induction temperatures as well as in a Haclp deficient yeast strain. All three strategies resulted in 20-5-8 which had the highest fluorescence among all the scaffolds evolved. Panel B is a set of ribbon diagrams of dual loop inserted GFP indicating the mutations from each round of evolution. (round 1: pink; round 2: green; round 3: yellow; round 4: brown. Loop regions 102-103 and 172-173 with surrogate binding loops are in red and blue respectively.)

Directed Evolution of a Family of Scaffolds that can Accommodate Dual Loop Insertion We hypothesized that evolution of the GFPM-H3L3 dual surrogate loop-inserted scaffold for improved fluorescence and expression would yield a better-folded and processed GFP scaffold capable of accommodating a diverse loop repertoire. Since GFP requires correct folding to become fluorescent (Reid B G & Flynn G C, *Biochemistry,* 36:6786-6791, 1997) and very little nonfluorescent GFPM-H3L3 protein makes it through the yeast secretory pathway to the cell surface (FIG. 1B), the secretory quality control machinery provided a reasonable filter that limited the export of proteins lacking an intact chromophore environment. Thus, the folding and processing fitness of GFPM-H3L3 was used as a convenient selection criterion. Scaffolds were mutagenized while keeping the inserted surrogate loops free of mutation (FIG. 6). Then, scaffolds that were both fluorescent and displayed were selected using a combination of two induction conditions over four rounds of directed evolution. A scheme of the directed evolution is shown in FIG. 9.

TABLE 3

Mutations in the monomeric yEGFP sequence encountered in the scaffolds evolved in this study

| | Clones | | | | | | | | | | |
|---|---|---|---|---|---|---|---|---|---|---|---|
| Mutations | 20-1-3 | 20-1-6 | 20-1-8 | 20-2-7 | 37-2-1 | 37-2-4 | 37-2-7 | 70C-3 | 20-4-8 | 20-5-8 | D20-5-1 |
| K3E | x | | | | | | | | | | |
| D19N | x | x | x | x | x | x | x | x | x | x | x |
| K26E | | | x | | | | | | | | |
| Y39H | | | | | | | x | x | x | x | x |
| F64L | x | x | x | x | x | x | x | x | x | x | x |
| A87T | x | x | x | x | x | x | x | x | x | x | x |
| N105T | | | | | | | | | | x | x |
| D117G | | | | | | | | | | x | x |
| Y151C | | | | | | | | x | | | |
| V163A | | | | | x | x | x | x | x | x | x |
| E172K | | | | | x | | | x | x | x | x |
| D190N | | | | | | x | | | | | |
| N198D | | | | | | x | | | | | |
| Q204R | | | | | | x | | | | | |
| K206I | | | | x | | | | | | | |
| L221V | | | | | | | | | x | x | x |
| F223S | | | | | | | | | | | x |
| K238E | | | | | | | x | | | | |

For directed evolution rounds 1-4, scaffold libraries were selected after display induction at 20° C. since it has been shown previously that it is the optimum temperature for soluble expression of unmodified GFP using yeast (Huang D & Shusta E V, *Biotechnology Progress,* 21:349-357, 2005). In parallel to 20° C. selections, for directed evolution rounds 2-4, the library was also selected after induction at 37° C. to apply a more restrictive selection pressure that requires the scaffold to be properly folded and processed even at a temperature that has been shown to have deleterious effects on yeast expression for unmodified GFP (Huang D & Shusta E V, *Biotechnology Progress,* 21:349-357, 2005).

From the first round, three unique clones 20-1-3, 20-1-6, and 20-1-8 were obtained that exhibited improved fluorescence or expression or both (Table 3 and FIG. 1C, compare to GFPM-H3L3). Among these three, clone 20-1-6 had three mutations: D19N, F64L, and A87T, all of which were conserved in 20-1-3 and 20-1-8 (Table 3).

Figure 11:
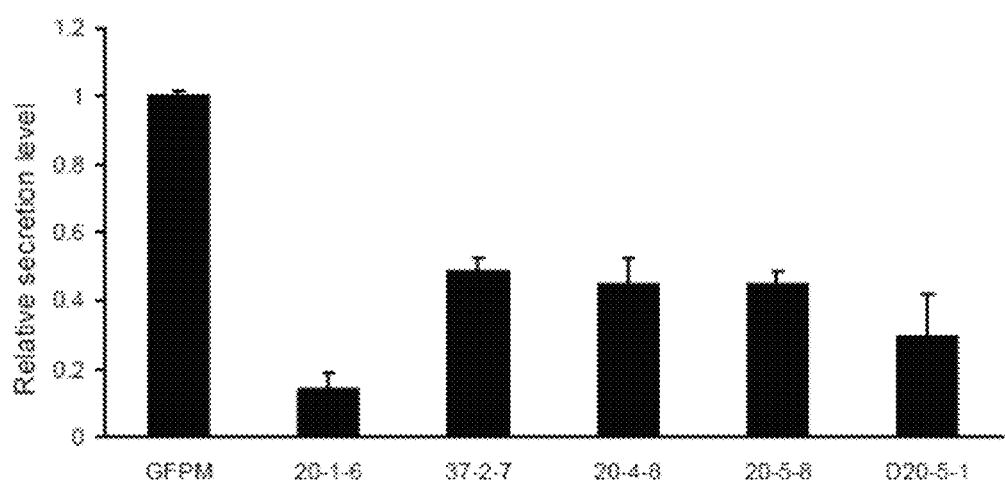
FIG. 11 is a bar graph disclosing soluble expression of the scaffolds evolved in this study. BJ5464 cells harboring pRS 316 variants of GFPM, clone 20-1-6, 20-2-7, and 37-2-7 were used to secrete protein at 20° C. Secreted protein was detected by Western blotting. Each data point represents triplicate samples. The western blot indicates the relative expression level of the scaffold evolved in this study. 20-1-6 had 10% the soluble expression level of GFPM. All scaffolds evolved beyond that were expressed at about 50% the level of GFPM (Since GFP and GFPM expression levels were indistinguishable, we estimated the scaffolds to be expressed at about 1 mg/lit using yeast).

To further improve the fluorescence and expression of the dual loop-inserted scaffold, the DNA sequences corresponding to 20-1-3, 20-1-6, and 20-1-8 were shuffled and mutated to obtain a second generation library of dual loop-inserted scaffolds. The best performing clones resulting from the second round, 37-2-1 and 37-2-7, were derived from the 37° C. selection scheme. Of the second round mutants, clone 37-2-7 had the highest external GFP fluorescence yielding fluorescence per molecule (GFP/c-myc) 28% that of unaltered GFPM, with substantially improved cell surface expression, which translated to much improved soluble secretion levels as well (FIG. 11). Comparison of the mutations found in 37-2-7 to 20-1-6 indicated the conservation and importance of all 20-1-6 mutations plus the presence off two additional mutations, Y39H and V163A (Table 3). The GFP fluorescence per molecule was a bit lower for 37-2-7 than 20-1-6 indicating the additional mutations were primarily "expression mutations" (FIG. 1C). After additional mutagenesis of 37-2-1 and 37-2-7, the best clone from the third round of directed evolution, 20-4-8, arose from the 20° C. selection and had approximately 2-fold increased fluorescence/molecule to reach 50% of the non-loop inserted GFPM parent (FIG. 1C). The mutant consisted of the combination of 37-2-1 and 37-2-7 mutations along with an additional mutation L221V. The best final round clone derived using 20-4-8 as a mutagenesis template, 20-5-8 (N105T and D117G), was identified in both the 20° C. and 37° C. sorts and possessed 60% of the fluorescence per molecule of GFPM (FIGS. 1C and 1D). To confirm that our yeast surface measurements of improved fluorescence/molecule correlated with improved function of soluble protein, we measured the corresponding brightness of GFPM, 37-2-7 and 20-5-8 as soluble, purified proteins. Indeed the fluorescence per molecule values of the soluble scaffold proteins correlated well with those measured on the yeast cell surface with 37-2-7 at 37% of GFPM (28% on surface) and 20-5-8 at 66% of GFPM (60% on surface) (Table 4).

TABLE 4

Spectral properties of selected scaffolds and GFAbs as soluble proteins.

| GFP variant | Quantum yield ($\Phi$) | Extinction coefficient ($M^{-1}cm^{-1}$) | GFP/mol (% of GFPM)$^a$ | GFP/mol (% of scaffold)$^b$ |
|---|---|---|---|---|
| GFPM | 0.60 | 37,000 | 100 | |
| 37-2-7 | 0.39 | 21,000 | 37 | |
| 20-5-8 | 0.73 | 20,000 | 66 | |
| G6 | 0.72 | 25,000 | 82 | 120 |
| T5 | 0.65 | 21,000 | 62 | 170 |
| T3 | 0.20 | 32,000 | 28 | 43 |
| 1.3 | 0.83 | 7,300 | 27 | 41 |
| 2.7 | 0.23 | 36,000 | 39 | 60 |

Figure 2:
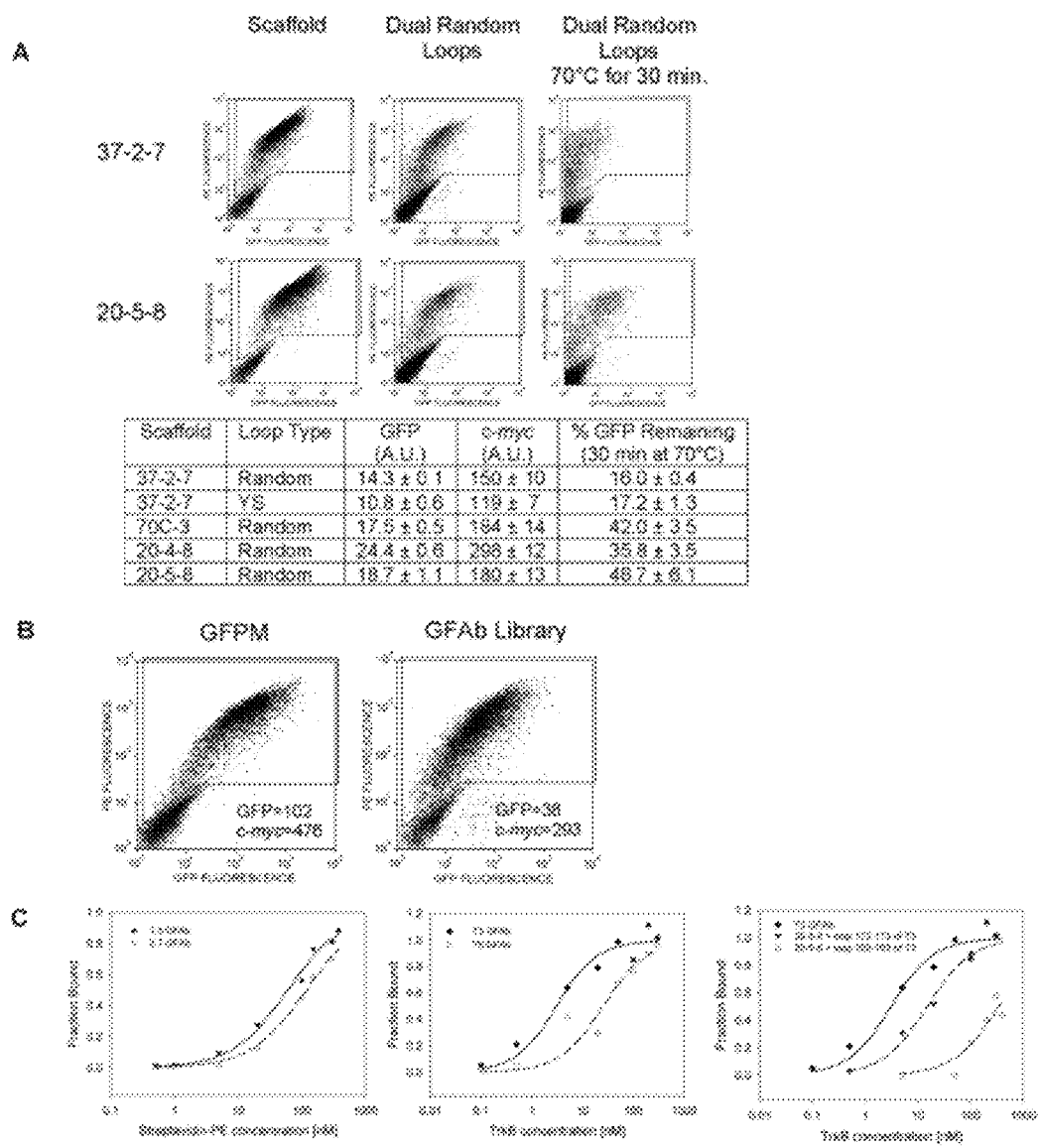
FIG. 2 discloses properties of random loop libraries and binding characteristics of isolated GFAb clones. Panel A is dot plots indicating the full-length expression (PE) and fluorescence (GFP) of two scaffolds, 37-2-7 and 20-5-8, the dual random loop libraries created using these scaffolds as well as the resistance to thermal denaturation of the resultant libraries. Quantification of the gated regions in the dot plots was performed for all scaffolds and the data compiled in the accompanying table. All data are the result of duplicate independent library and denaturation samples. For comparison, trends in scaffold properties can be found in FIG. 1C and FIG. 5. Panel B shows comparison of the fitness of the GFAb library with that of non loop-inserted GFPM. Fluorescence (GFP) and expression (c-myc) statistics can be found in the inset. Panel C shows yeast cell surface affinity titrations for selected GFAbs binding to Streptavidin-PE (left) or TrkB (center). Yeast cell surface affinity titrations for single loop knock-ins of TrkB-binding T3 GFAb indicating contribution of both inserted loops to the binding affinity of the dual loop T3 GFAb (right). Shown are single sample titrations and equilibrium binding fits, while $K_D$ with associated error from triplicate titration samples can be found in Table 6.
Figure 5:
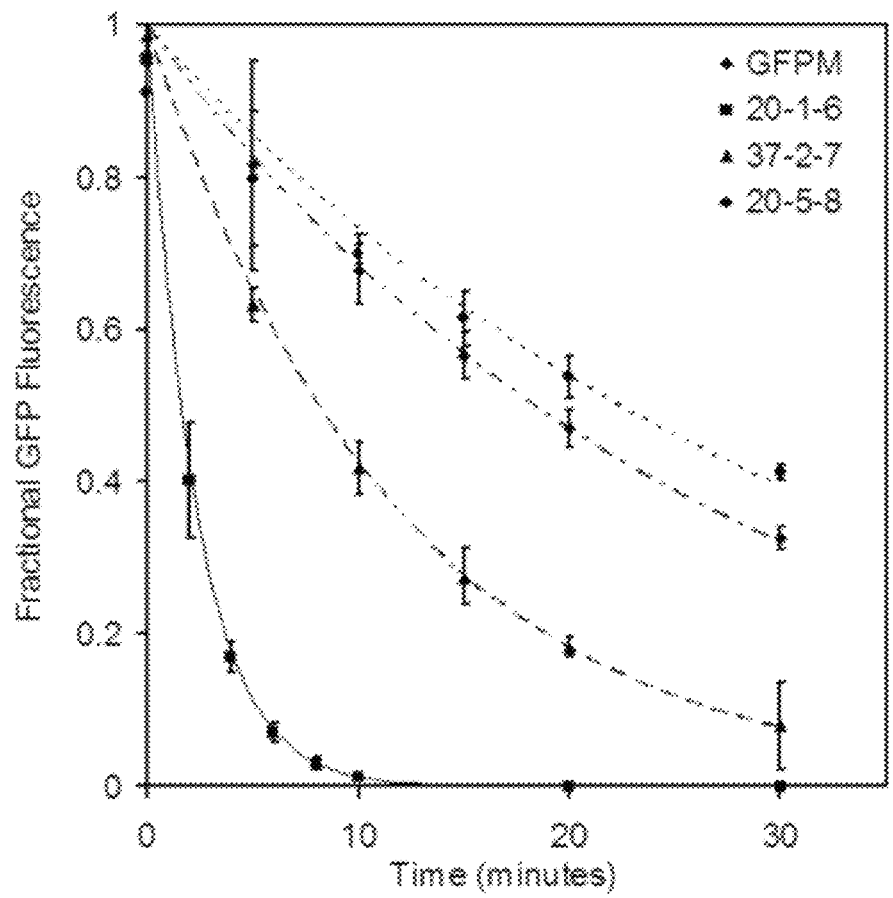
FIG. 5 discloses thermal denaturation characteristics of the evolved scaffolds. Scaffolds were denatured on the yeast surface for the indicated times at 70° C. and remaining fluorescence quantified by flow cytometry. First order exponential denaturation rate constants were determined and the exponential fits along with experimental data are shown in the plot. Rate constants are listed in the accompanying table along with the fluorescence half-life for each mutant (Half-life surface). The data represent triplicate samples throughout the entire timecourse. A similar procedure was performed with several of the purified, soluble scaffold proteins with fluorescence half-life monitored by 70° C. denaturation in solution using a thermocyler equipped with fluorescence detection capability (Half-life soluble).

In addition to evolving folding and expression competence by 20° C. and 37° C. selections, it was hypothesized that direct selection of a more thermally stable surrogate loop-inserted scaffold could aid the maintenance of structural integrity by stabilizing the β-barrel fold and chromophore environment leading to improved protein folding and processing. Thus, for the third round of directed evolution, using 37-2-1 and 37-2-7 as the templates for additional mutagenesis, a selection for loop-inserted scaffolds having increased resistance to thermal denaturation at 70° C. was also performed. The 70° C. selection, while yielding a significantly more thermally resistant scaffold, 70C-3 (half-life=21 min), failed to significantly improve GFP fluorescence and expression properties above the 37-2-7 parent (half-life=9 min) (FIG. 1C and FIG. 5). In contrast, the less stable 20-4-8 (half-life=18 min) scaffold that arose from the same 37-2-1 and 37-2-7 parents via the 20° C. selection had substantially improved properties (FIG. 2A and FIG. 5). Interestingly, even from the 20° C. and 37° C. selections, there was a distinct trend toward scaffolds that along with improved fluorescence and expression, also exhibited gains in thermal stability matching or exceeding non loop-inserted GFPM (FIG. 5). Taken together, it appears that improved scaffold fluorescence and expression required an improvement in thermal stability, but improved thermal stability alone does not guarantee improved scaffold fluorescence or expression. Thus, the secretory pathway of yeast is providing an additional selection criterion that can help sample segments of the fitness landscape not wholly substituted by a single biophysical property such as resistance to thermal denaturation. All round 2-4 scaffolds were produced as soluble fluorescent proteins at levels between 45-55% of GFPM, corresponding to 1.3-1.6 mg/L (FIG. 1C), and thus represent potential scaffolds for dual random loop insertion in that they are expressed on the yeast surface and can be solubly produced as fluorescent proteins.

Since interactions of dual loop-inserted scaffolds with the secretory machinery play important roles in the fluorescence and expression properties of the evolved scaffolds, it was further hypothesized that reduction of these potential interactions, while still selecting for improved fluorescence and expression in evolved scaffolds, would yield dual loop-inserted scaffolds more capable of folding and processing through the secretory pathway. To this end, selection in the final round of directed evolution, in addition to 20° C. and 37° C. selections, was performed using a yeast display strain deficient in the unfolded protein response (UPR) (FIG. 9). The UPR can be induced when the folding capacity of the endoplasmic reticulum is exceeded and unfolded proteins accumulate in the ER. The transcription factor Hac1p acts as a primary regulator of the UPR by activating a broad transcriptional response that alleviates the stress of protein folding/misfolding and protein accumulation. We have also shown previously that yeast strains with a HAC1 deletion have increased intracellular accumulation of GFP. Importantly, UPR activation can lead to upregulation of chaperones and foldases in addition to upregulation of molecules acting in very diverse pathways in the cell, including links to the quality control machinery through ERAD, secretory trafficking, cell wall remodeling, and distal secretion.

Thus, we tested whether the fluorescent display of the 20-4-8 scaffold was affected by a Δhac1 display strain. Interestingly, while non loop-inserted GFPM did not exhibit a change in external GFP fluorescence or expression in the Δhac1 strain, 20-4-8 had a decreased fluorescence/molecule in the Δhac1 strain (FIG. 10), indicating a folding deficiency for this protein in the absence of a functioning UPR. Thus, since a functioning UPR proved important for effective 20-4-8 processing, disruption of the UPR provided a convenient selection pressure. Moreover, for both non loop-inserted GFP and 20-4-8, intracellular accumulation was increased by roughly 2-fold as was seen previously for Δhac1 yeast GFP secretion strains (data not shown). Thus, a two-step selection was performed that first identified 20-4-8 mutants that have increased fluorescence and surface expression in the Δhac1 secretion strain. Immediately, the selected clones were subjected to a second sort to choose those mutants that also had the lowest levels of intracellular accumulation (see methods for details).

Two mutants displaying significant improvement in their Δhac1 phenotype were identified. The first, 20-5-8, was also identified in both of the parallel 20° C. and 37° C. sorts because it possessed better fluorescence per molecule and external fluorescence levels under all sort conditions (FIG. 10). Unlike the scaffolds from rounds 1-3, the additional 20-5-8 mutations (N105T and D117G) did not yield a coordinate increase in stability. While the per molecule fluorescence was improved under the Δhac1 conditions compared with the 20-4-8 parent, it was still lower than that seen in the intact UPR parent strain, and thus a folding deficiency remained. By contrast, the Δhac1 selections also yielded a mutant, D20-5-1, that corrected the 20-4-8 folding deficiency in that it restored the per molecule fluorescence in the Δhac1 strain to that seen for 20-4-8 in the wild-type yeast strain (FIG. 10). Interestingly, in the presence of a normally functioning UPR, D20-5-1 was indistinguishable from the 20-4-8 parent indicating that an intact UPR provides enough folding and processing capacity such that an improved folding/processing mutant as defined by performance in the absence of UPR effects, does not aid overall yield or folding fidelity. All scaffolds were produced as soluble proteins with HL-6 having only 15% of the secreted yield as that of non loop-inserted GFPM, as suggested by its low cell surface expression. All other scaffolds were produced fairly uniformly at levels between 45-55% of GFPM, corresponding to 1.5-2 mg/L, and thus represent potential scaffolds for dual loop insertion in that they are expressed on the yeast surface, are fluorescent, and can be solubly produced at reasonable levels.

Table 5: Removed

Development of Dual Random Loop GFPM Libraries

The next step of the study was to determine whether the surrogate loop-evolved scaffolds could accommodate amino acid diversity at both positions simultaneously. We also wished to determine how the various scaffolds having differing stability, fluorescence, and expression properties affected the quality of the resultant libraries in terms of expressed diversity and overall fitness.

For each scaffold, the inserted loop regions were replaced by loops of the same length (8 amino acids at 172-173 and 9 amino acids at 101-102) that had been randomized using the NNK oligonucleotide method (See Methods for details, FIG. 6). The expressed diversity of the dual random loop libraries built into 37-2-7, 70C-3 and 20-4-8 scaffolds was indistinguishable. When corrected for stop codon probability and the negative displaying yeast population lacking plasmid (Rakestraw A & Wittrup K D, Biotechnology and bioengineering, 93:896-905, 2006), approximately 70% of the dual random loop-inserted GFPs not containing stop codons are displayed on the surface and possess fluorescence above background (FIG. 2A). Interestingly, although an improvement in thermal stability occurred when evolving 37-2-7 to 70C-3 and 20-4-8 (FIG. 5), there was no effect on the expressed diversity.

However, the stability, folding and processing attributes of the scaffold do appear to play an important role in library fitness for the expressed clones since the aggregate fluorescence, expression and stability properties of the libraries generally improve as the fitness of the scaffold improves (FIG. 2A and compare to scaffold trends in FIG. 1C). As an exception, the best scaffold in terms of fluorescence and expression properties, 20-5-8, only allowed 55% of the loop-inserted GFPs to be expressed. In addition, there was a drop in fluorescence and expression properties compared with the 20-4-8 library, indicating that gains provided by the evolution strategy may have been beginning to become specific to the amino acid content of the surrogate loops.

Finally, to test the scaffold capability of accommodating different forms of loop diversity, a dual loop library in the 37-2-7 scaffold was also created using randomized loops possessing only tyrosine and serine residues as these have been shown to allow minimalist design of binding sites (Koide A et al., Proc Natl Acad Sci USA, 104:6632-6637, 2007). Indeed, 37-2-7 also accommodated this form of diversity although the fluorescence and expression properties were a bit diminished compared with the fully randomized loops discussed above (FIG. 2A).

Selection and Characterization of Dual Loop-Inserted GFP Binders (GFAbs)

For the selection of binders to various antigens, we combined the various scaffold libraries discussed above to form a selectable library of high fitness. Using flow cytometry, we recovered the top 20% of clones in terms of both GFP fluorescence and expression. The resulting GFAb library had an expressed diversity of $6 \times 10^6$ clones having high fitness averaging 40% of the fluorescence and 60% of the expression of non-loop inserted GFPM (FIG. 2B). This library was used for all binding selections discussed below.

As proof-of-concept selections, binders against streptavidin-phycoerythrin and biotin-phycoerythrin conjugates were selected by flow cytometry and several unique GFAbs were recovered against each target and affinity titrations on the surface of yeast yielded binding dissociation constants from 70 nM to micromolar (FIG. 2C and Table 6).

TABLE 6

Expression, fluorescence and binding properties of selected GFAb clones.

| Target | GFAb | Scaffold | Loop 102-103 | Loop 172-173 | $K_D$ (nM)$^a$ | Expression (% of scaffold)$^f$ | GFP/c-myc (% of scaffold)$^f$ | Secreted Yield (% of scaffold)$^h$ | GFP/mol (% of scaffold)$^i$ |
|---|---|---|---|---|---|---|---|---|---|
| TrkB | T1 | 37-2-7 | SKSRSLESV (SEQ ID NO: 29) | GYLRWLFG (SEQ ID NO: 30) | 60 | 79 ± 5 | 140 ± 20 | | |
| | T3 | 20-5-8 | VINPFTVRS (SEQ ID NO: 31) | NAWVVHRR (SEQ ID NO: 32) | 3.2 ± 0.7 | 66 ± 4 | 77 ± 10 | 20 [0.30] | 43 |
| | T5 | 37-2-7 | PSWWSLFFP (SEQ ID NO: 33) | STATGLFA (SEQ ID NO: 34) | 29 ± 4 | 78 ± 4 | 160 ± 30 | 24 [0.32] | 170 |
| GAPDH | G6 | 20-5-8 | RVSRFLLTT (SEQ ID NO: 35) | KSRIISSQ (SEQ ID NO: 36) | 18 ± 6$^g$ | 99 ± 7 | 73 ± 11 | 80 [1.1] | 120 |

TABLE 6-continued

Expression, fluorescence and binding properties of selected GFAb clones.

| Target | GFAb | Scaffold | Loop 102-103 | Loop 172-173 | $K_D$ (nM)[a] | Expression (% of scaffold)[f] | GFP/c-myc (% of scaffold)[f] | Secreted Yield (% of scaffold)[h] | GFP/mol (% of scaffold)[i] |
|---|---|---|---|---|---|---|---|---|---|
| | G7[b] | 20-5-8 | NVIYPFLYA (SEQ ID NO: 37) | RVTKTKHK (SEQ ID NO: 38) | >500 | | | | |
| | G4[b] | 20-5-8 | RGVSKSFLL (SEQ ID NO: 39) | QGITKGYK (SEQ ID NO: 40) | >500 | 130 ± 20 | 91 ± 31 | | |
| | G8[b] | 20-5-8 | SHCLFRKCY (SEQ ID NO: 41) | ARSIRMKV (SEQ ID NO: 42) | >500 | 140 ± 20 | 51 ± 18 | | |
| Strep-PE | 1.3[c] | 20-5-8 | AISRSFFST (SEQ ID NO: 43) | IRNLKYTN (SEQ ID NO: 44) | 70 ± 11 | 120 ± 10 | 67 ± 15 | 140 [1.9] | 41 |
| | 2.7[d] | 20-5-8 | VFSSLRYHV (SEQ ID NO: 45) | LRMDDTNP (SEQ ID NO: 46) | 140 ± 20 | 96 ± 7 | 61 ± 11 | 120 [1.6] | 60 |
| | 2.17[d] | 20-5-8 | KARMRLFLM (SEQ ID NO: 47) | EYGDTLLS (SEQ ID NO: 48) | 110 | 85 ± 6 | 27 ± 6 | | |
| Biotin-PE | 2[e] | 20-5-8 + E115K | RGLFWPVLI (SEQ ID NO: 49) | PNPVFRQN (SEQ ID NO: 50) | 1400 | 58 ± 4 | 37 ± 9 | | |
| | 5[e] | 20-5-8 | SCSWCLFTL (SEQ ID NO: 51) | KNQMGMGK (SEQ ID NO: 52) | 260 | 52 ± 3 | 47 ± 8 | | |
| | 12[e] | 37-2-7 | KSHFTIFRT (SEQ ID NO: 53) | DGWRRTTV (SEQ ID NO: 54) | 250 | 87 ± 7 | 56 ± 8 | | |
| | 16[e] | 20-5-8 | NCRWCTYYL (SEQ ID NO: 55) | STSNWMRM (SEQ ID NO: 56) | 190 | 56 ± 7 | 25 ± 5 | | |

[a] $K_D$ ± SD reported for triplicate titrations on yeast surface, otherwise $K_D$ from single sample titration reported.
[b] Clone binds both GAPDH and streptavidin phycoerythrin.
[c] Clone binds streptavidin alone.
[d] Clone requires presence of both streptavidin and PE.
[e] Clone binds PE alone.
[f] Expression (c-myc) and fluorescence (external GFPl c-myc) properties measured on yeast surface normalized to the parent scaffold.
[g] Represents affinity estimate based on low concentration binding data as binding at higher concentrations (>100 nm) of GAPDH antigen exhibit the hook effect with decreased binding signal
[h] Values in brackets represent non-optimized shakeflask yields in mg/L.
[i] GFP per molecule (brightness) for the soluble protein defined as the extinction coefficient x quantum yield. Brightness values are normalized to parent scaffold to show the effects of changes in loop sequence. Detailed values for extinction coefficient and quantum yield can be found in Table 4.

Next, GFAbs were raised against the monomeric extracellular domain of a neurotrophin receptor (TrkB) and against glyceraldehyde 3-phosphate dehydrogenase (GAPDH). While GAPDH-binding GFAbs bound in the 18-500 nM range, GFAbs specific to TrkB gave monomeric binding dissociation constants as low as 3.2 nM (FIG. 2C and Table 6). Moreover, although no counterselections were performed to fine-tune specificity, binding of the high affinity T3 GFAb to two other tyrosine kinase neurotrophin receptors (TrkA and TrkC) having high homology to TrkB was not detected, indicating the capability for identifying isoform-specific GFAbs (data not shown). As a whole, GFAb clones had properties ranging from 25-160% of the displayed fluorescence/molecule of the parent scaffold, and surface expression levels ranged from 50-150% of the scaffold (Table 6).

We also examined whether both loops in the putative binding interface contributed to the binding affinity of the selected clones. To accomplish this task, we individually grafted the binding loops for T3 back into the 20-5-8 scaffold such that single-loop GFAbs were created with the second loop being the surrogate loop. Affinity titrations of the single binding loop variants were performed on the yeast surface and indicated that both loops contribute to the observed binding affinity. While the 20-5-8 scaffold possesses no binding affinity towards TrkB, addition of the 172-173 loop yields a GFAb with 300 nM binding affinity, addition of the 102-103 binding loop yields a GFAb of 19 nM affinity, while both loops as in the original T3 GFAb yield 2 nM affinity (FIG. 2C). The analogous constructs were also created for the G6 GFAb that binds GAPDH with titrations again indicating dual loop contribution to binding (data not shown).

Figure 3:
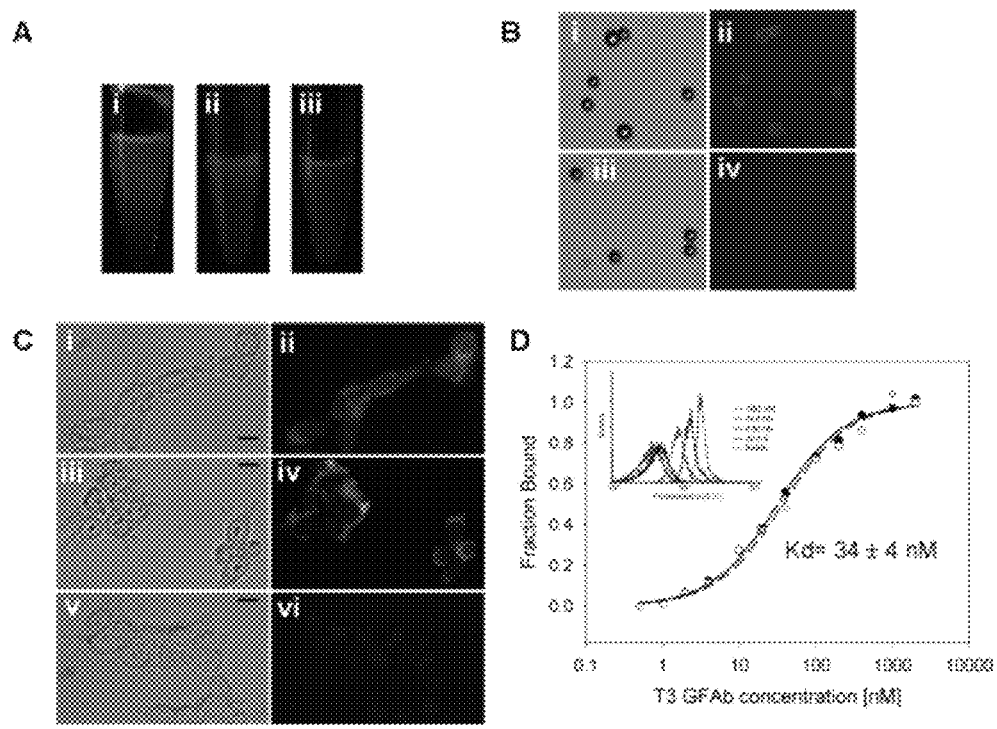
FIG. 3 discloses properties of soluble, purifies GFAbs. (A) Samples of purified protein illuminated with a hand-held UV lamp indicating the presence of fluorescent protein: i) GFPM, ii) 20-5-8 and iii) G6 GFab. (B) Streptavidin-coated polystyrene beads were labeled with streptavidin-PE binding 1.3 GFab (i and ii) or its parent scaffold 20-5-8 (iii and iv) and imaged fluorescence microscopy. (C) Permeabilized HEK-293 cells were incubated with: (i and iii) GAPDH binding G6 GFab, (iii and iv) and anti-GAPDH antibody followed by fluorescent Alexa488 secondary antibody, and (v and vi) the parent scaffold 20-5-8, and cells were monitored for green fluorescence (GFab-derived: I, ii, v, and vi or Alexa488-derived: iii and iv). DAPI was used to stain the nucleus (blue). (Scale bar, 20 µm.) (D) Affinity titration for secreted T3 GFab on TrkB-loaded beads. Binding-dependent GFab fluorescence was monitored by flow cytometry as a function of T3 concentration to generate a binding curve and associate $K_D$. Representative flow cytometry histograms for various T3 dilutions are presented in the Inset. Also shown are no GFab, bead-only controls, and the negligible binding of parent scaffold 20-5-8 to TrkB-loaded beads. Beads loaded with irrelevant antigen and labeled with T3 also exhibited negligible binding mirroring that shown for 20-5-8. Data from duplicate samples are depicted as open and filled circles along with their associated equilibrium binding model fits.

To further characterize the GFAbs, five were secreted from yeast and purified yields ranged from 0.3-2 mg/L (Table 6). All soluble, purified proteins retained fluorescence with per molecule values ranging from 40-120% of the parent scaffold (FIG. 3A and Table 4). Moreover, the purified GFAbs possess binding activity as demonstrated by several fluorescent labeling assays. Streptavidin-PE binding 1.3 GFAb specifically labeled streptavidin-linked beads with a fluorescent signal discernable from the parent scaffold (FIG. 3B), and binding could be competed with soluble streptavidin-PE antigen (data not shown). In addition, the G6 GAPDH-binding GFAb was used as a single step reagent to detect GAPDH present in the cytoplasm of HEK-293 cells (FIG. 3C). Finally, purified and soluble T3 GFAb was used in combination with TrkB-loaded beads and FACS for detailed binding affinity measurement. Using solely the intrinsic fluorescence that results from T3 GFAb binding to the TrkB-loaded beads, the binding affinity of the soluble T3 GFAb was determined to be 34 nM (FIG. 3D). The nanomolar binding affinity of soluble T3 GFAb was also further confirmed by a solution phase competition assay where both the T3 and TrkB were in soluble form (see Methods for details). In summary, for each of the four targets there was at least one GFAb clone with a solid combination of affinity, fluorescence, and expression properties, indicating the ability to isolate useful lead molecules from the high fitness dual loop-inserted GFP library.

Discussion

In this investigation, we demonstrate that it is possible to create fluorescent dual-loop inserted GFAb scaffolds capable of binding to various antigens with nanomolar affinity.

Examination of the mutations in the evolved scaffolds reveals some crossover with mutants previously identified to impart fluorescence and stability to GFP (Table 3). The mutation F64L has been uncovered while evolving GFP for higher fluorescence when produced in *E. coli*, and the mutation improves the fluorescence per molecule in addition to shifting the excitation maximum to 488 nm (Cormack B P et al., *Gene*, 173:33-38, 1996). The same study yielded the S65G and S72A mutations used in our enhanced GFPM starting template. Moreover, our selection for improved fluorescence per molecule was performed using an excitation of 488 nm, suggesting how the F64L mutation may function. DNA shuffling was previously used to improve the fluorescence of GFP largely by increasing solubility in bacteria, and the cycle 3 mutant identified in that study included the mutation V163A (Crameri A et al., *Nature Biotechnology*, 14:315-319, 1996). The V163A mutant is present in all of our dual loop library scaffolds and was likely isolated because the selection pressure used here included improved folding and processing through the yeast secretory pathway which could be a function of solubility. Another relevant comparison is the superfolder GFP that has been used quite extensively in binding loop insertion studies as described in the introduction. This protein was raised by attaching GFP to an insoluble protein (H-subunit ferritin) and evolving the GFP for enhanced fluorescence and solubility of the complex when expressed in *E. Coli* (Pedelacq J D et al., *Nature Biotechnology*, 24:79-88, 2006).

In addition to F99S, M53T, V163A, F64L and S65T present in the superfolder starting template, six new superfolder mutations: S30R, Y39N, N105T, Y145F, I171V, and A206V were introduced that improved the forward folding kinetics of GFP and its chemical stability. Of the six superfolder mutations, Y39N(Y39H this study) and N105T are found in our scaffolds. Interestingly, these two mutations appeared to function differently in superfolder GFP, Y39N improved refolding kinetics, while N105T improved refolding stability, both of which could be argued to assist processing through the yeast secretory pathway.

In addition, there exist five scaffold mutations (A87T, D19N, E172K, L221V and D117G), two of which were found in the very first round of directed evolution, that to our knowledge have not been reported as assisting fluorescence or expression properties of GFP or its variants. It is interesting to note that 2 of these mutations, A87T and D117G, along with N105T, are located in or near turns involved in the two beta strands that are part of the Asp102-Asp103 insertion position that was most deleterious upon surrogate loop insertion (FIGS. 2B and 3B). Another of these mutations E172K is part of the Glu172-Asp172 loop insertion site (FIGS. 2B and 3B). Thus, these additional mutations are likely partially a consequence of the filter provided by the advanced secretory pathway of yeast that was an important part of the selection procedure, and partially a result of our approach to engineer a dual loop-compatible scaffold using the surrogate loop approach.

Yeast display is well suited for the engineering of fluorescent proteins because it is possible to select libraries using antigen and GFAb fluorescence as dual simultaneous criteria. This approach therefore results in selection of only fluorescent binders, something that could not be guaranteed using phage display without the aid of labor-intensive secondary confirmations (Kiss C et al., *Nucleic Acids Research*, 34:15, 2006). Moreover, while there is not a perfect quantitative agreement between surface-displayed and secreted GFAb stability, fluorescence and binding properties (FIG. 1C, FIG. 3D, FIG. 5, Table 4), surface display fitness of GFAbs certainly correlates with GFAbs that can be produced solubly while maintaining solid fluorescence and binding properties.

The GFAb affinities for the selected clones ranged from low nanomolar to micromolar and were similar to those seen for binding clones isolated from other nonimmune antibody and alternative scaffold libraries (Lipovsek D et al., *Journal of Molecular Biology*, 368:1024-1041, 2007; Feldhaus M J et al., *Nature Biotechnology*, 21:163-170, 2003; Wang X X et al., *Nat Methods*, 4:143-145, 2007). Interestingly, compared to the highest affinity single loop-inserted GFP binder previously reported (470 nM) (Dai M et al., *Protein Engineering Design & Selection*, 21:413-424, 2008), the dual loop scaffold appeared capable of providing an extra level of binding affinity as loop swapping experiments with two individual clones selected against different antigens indicated that each loop contributed to the measured $K_D$ value.

Moreover, it is expected that standard evolutionary techniques could be used to fine-tune the specificity, affinity and fluorescence properties of our lead GFAb molecules as desired. Although we constrained the randomized loop length to that of the surrogate loops for our lead library, it may prove useful for the fine-tuning of GFAb properties to include a component of loop length diversity as this approach has proven fruitful for antibody affinity maturation and for artificial scaffold maturation (Koide A et al., *Proc Natl Acad Sci USA*, 104:6632-6637, 2007; Hackel B J et al., *J Mol Biol*, 381:1238-1252, 2008. Moreover, although the extracted GFAb binders were all from the NNK-based loop libraries rather than the binary code YS library, further refinement of the amino acid content of the binding loops could also be a target for library optimization (Gilbreth R N et al., *J Mol Biol*, 381:407-418, 2008).

Finally, successful development dual-loop GFAb scaffolds could enable a wide range of other applications given the range of GFP spectral variants that have been developed (Zhang J et al., *Nat Rev Mol Cell Biol*, 3:906-918, 2002), and the surrogate loop approaches used here could in principle be applied to other structurally homologous fluorescent proteins like the monomeric red fluorescent protein family (Shaner N C et al., *Nat Biotechnol*, 22:1567-1572, 2004).

Materials and Methods

Strains and Media

Surface display was performed using the standard surface display yeast strain EBY100 (MATa AGA1::GAL1-AGA1:: URA3 ura3-52 trp1 leu2Δ1 his3Δ200 pep4::HIS3 prb1Δ1.6R can1 GAL). *Saccharomyces cerevisiae* strain BJ5464 (MATα ura3-52 trp1 leu2Δ1 his3Δ200 pep4::HIS3 prb1Δ1.6R can1 GAL) was used for protein secretion. Yeast cells were grown in minimal SD-CAA medium (20 g/L dextrose, 6.7 g/L yeast nitrogen base, 5 g/L casamino acids, 10.19 g/L Na$_2$HPO$_4$.7H$_2$O, 8.56 g/L NaH$_2$PO$_4$.H$_2$O) and protein display or secretion was induced using SG-CAA (20 g/L galactose replacing dextrose). Bovine Serum Albumin (BSA) was added at 1 g/L as a non-specific carrier for protein secretion studies. The *Escherichia coli* strains XL1-Blue (Stratagene, La Jolla, Calif., USA) and DH5a (Invitrogen, Carlsbad, Calif., USA) were used for molecular cloning. Luria-Bertani medium (10 g/L tryptone, 5 g/L yeast extract, 10 g/L NaCl, pH 7.5, 50 µg/ml ampicillin) was used for bacteria growth and plasmid amplification.

Plasmids

Starting with pRS 316-yEGFP (Huang D & Shusta E V, *Biotechnology Progress*, 21:349-357, 2005) which encodes a yeast codon-optimized variant of GFP (yEGFP) that also possesses the fluorescence enhancing mutations S65G and S72A (Cormack B P et al., *Gene*, 173:33-38, 1996), site directed mutagenesis (Strategene, La Jolla, Calif., USA) was used to change alanine at position 206 to lysine to convert yEGFP into its monomeric form (Zacharias D A et al., *Science*, 296:913-916, 2002) (GFPM), and this plasmid was denoted pRS 316-GFPM (see Table 7 for primers used). Next, insertion mutagenesis (Strategene, La Jolla, Calif., USA) was utilized to insert two unique restriction sites AflII and SpeI between amino acids Asp102-Asp103 to give pRS 316-GFPM-AS (Table 8). Two more unique restriction sites, XbaI and MluI, were inserted between amino acids Glu172-Asp173 to yield the plasmid pRS 316-GFPM-XM. Insertion of restriction sites at both locations resulted in the plasmid pRS 316-GFPM-ASXM. These open reading frames were then transferred to the pCT yeast surface display plasmid using NheI and BamH1 restriction sites (Huang D & Shusta E V, *Biotechnology Progress*, 21:349-357, 2005). Synthesized oligonucleotides (IDT DNA, Coralville, Iowa, USA) encoding the 9 amino acids of CDRL3 and 8 amino acids of CDRH3 from the single-chain D1.3 antibody (Bajorath J et al., Journal of Biological Chemistry 270, 22081-22084, 270:22081-22084, 1995) were inserted at positions Asp102-Asp103 and/or Glu172-Asp173, respectively to yield three more plasmids: pCT-GFPM-ASL3, pCT-GFPM-XMH3, and pCT-GFPM-H3L3 (Table 8). Finally, pCT-GFPM-H3L3 was transferred to the pCT-ESO plasmid using NheI and BamH1 restriction sites as this plasmid is better suited for library mutagenesis (Piatesi A et al., *Protein Expression and Purification*, 48:232-242, 2006).

Scaffold and Dual Random Loop Library Creation

To create the scaffold libraries, the inserted loop regions were kept constant while the remaining GFPM scaffold was mutated (see FIG. 6 for schematic, Table 7 for primers used). To create the dual random loop libraries, the scaffold including the added restriction sites was left unaltered while the 9 amino acids inserted at Asp102-Asp103 and the 8 amino acids inserted at Glu172-Asp 173 were simultaneously randomized using the NNK method (see FIG. 6 for schematic, Table 7 for primers used). Details are disclosed below.

TABLE 7

Oligonucleotides employed for library construction.

| | Oligonucleotide name | DNA sequence 5'->3' | SEQ ID NO |
|---|---|---|---|
| 1 | A206K upper | CTTATCCACTCAATCTAAGTTATCCAAAGATCCAAAC | 3 |
| 2 | A206K lower | GTTTGGATCTTTGGATAACTTAGATTGAGTGGATAAG | 4 |
| 3 | AflII-SpeI insertion upper | GAACTATTTTTTCAAAGATCTTAAGACTAGTGACGGTAACTAC | 5 |
| 4 | AflllI-SpeI insertion lower | CTGGTCTTGTAGTTACCGTCACTAGTCTTAAGATCTTTGAAAAA | 6 |
| 5 | XhoI-MluI insertion upper | CAAAATTAGACACAACATTGAATCTAGAACGCGTGATGGTTCT | 7 |
| 6 | XhoI-MluI insertion lower | GCTAATTGAACAGAACCATCACGCGTTCTAGATTCAATGTTGT | 8 |
| 7 | ESO forward | GTGGAGGAGGCTCTGGTGGAGGCGGTAGCGGAGGCGGAGGGTCGGCTAGC | 9 |
| 8 | ESO reverse | GAACAAAAGCTTATTTCTGAAGAGGACTTGTAATAGCTGAGATCTGATA | 10 |
| 9 | Upper CDRL3 | TTAAGCAACATTTTTGGAGTACTCCTCGGACGA | 11 |
| 10 | Lower CDRL3 | CTAGTCGTCCGAGGAGTACTCCAAAAATGTTGC | 12 |
| 11 | Upper CDRH3 | CTAGAGAGAGAGATTATAGGCTTGACTACA | 13 |
| 12 | Lower CDRH3 | CGCGTGTAGTCAAGCCTATAATCTCTCTCT | 14 |
| 13 | Random loop 102-103 | CTTGTAGTTACCGTCACTAGT (MNN)$_9$ CTTAAGATCTTTGAAAAAAT | 15 |
| 14 | Random loop 172-173 | AGACACAACATTGAATCTAGA (NNK)$_8$ ACGCGTGATGGTTCTGTTCAA | 16 |
| 15 | 102-103 overhang | ACTAGTGACGGTAACTACAAG | 17 |
| 16 | 172-173 overhang | TCTAGATTCAATGTTGTGTCT | 18 |

TABLE 7-continued

Oligonucleotides employed for library construction.

| Oligonucleotide name | DNA sequence 5'->3' | SEQ ID NO |
|---|---|---|
| 17 Light extension | AAACTTGACTTCAGCTCTGGTCTTGTAGTTACCGTCACTAGT | 19 |
| 18 Heavy extension | AATGGTATCAAAGCTAACTTCAAAATTAGACACAACATTGAATCTAGA | 20 |

TABLE 8

Plasmids created in this study.

| Plasmid name | Amino acid insertion between Asp102-Asp103 | Amino acid insertion between Glu172-Asp173 |
|---|---|---|
| GFPM-AS | LKTS (SEQ ID NO: 21) | — |
| GFPM-XM | — | SRTR (SEQ ID NO: 22) |
| GFPM-ASXM | LKTS (SEQ ID NO: 23) | SRTR (SEQ ID NO: 24) |
| GFPM-ASL3 | LKQHFWSTPRTTS (SEQ ID NO: 25) | — |
| GFPM-XMH3 | — | SRERDYRLDYTR (SEQ ID NO: 26) |
| GFP-H3L3 | LKQHFWSTPRTTS (SEQ ID NO: 27) | SRERDYRLDYTR (SEQ ID NO: 28) |

To create the scaffold libraries, the inserted loop regions were kept constant while the remaining GFPM scaffold was mutated (see FIG. 6 for schematic, Table 7 for primers used). Starting with pCT-ESO-GFPM-H3L3, three PCR reactions were carried out to amplify regions I, II, and III as indicated in FIG. 6. Each PCR reaction consisted of plasmid template (250 ng), 10 µM of dNTP mix (Invitrogen, Carlsbad, Calif., USA), 10× buffer (—MgCl$_2$), 50 mM MgCl$_2$, 1 µl of Platinum Taq (Invitrogen, Carlsbad, Calif., USA), and sterile water to bring the reaction volume to 50 µl. The reaction was carried out using a MJ Research PTC-200 thermocycler. The three PCR products were gel purified using a gel extraction kit (Qiagen, Valencia, Calif., USA) and 1 µl was utilized for a mutagenic PCR reaction. Mutagenesis was carried out by error-prone PCR using the nucleotide analogues 2'-deoxy-p-nucleoside-5'-triphosphate and 8-oxo-2'-deoxyguanosine-5'-triphosphate (TriLink Biotech, CA, USA) as described previously (Skerra A., Curr. Opin. Biotechnol., 18:295-304, 2007). The mutated fragments were subsequently amplified by PCR and 10 µl of each were used in a 100 µl primer-less PCR reaction to assemble the entire scaffold open reading frame. After gel purification and pellet paint precipitation, the amplified scaffold library was then created in yeast by homologous recombination with scaffold PCR product and pCT-ESO acceptor vector as described earlier (Lipovsek D et al., Journal of Molecular Biology, 368:1024-1041, 2007).

For the second round of directed evolution, the library was created by first shuffling first round clones 20-1-3, 20-1-6 and 20-1-8 followed by the above mutagenesis procedure to incorporate additional mutation. The third and fourth rounds involved only error-prone PCR as described above in the absence of shuffling.

The fluorescence of evolved GFP scaffolds measured by flow cytometry is contributed to by the GFP fluorescence from proteins inside the cell as well as from those being displayed on the surface of yeast. Thus, to verify that we were evolving the scaffold to be more fluorescent on the surface of yeast and/or expressed at higher levels on the surface and not just evolving an increase in intracellular retained fluorescent protein, the surface protein was stripped to determine the external fluorescence contribution for each clone. After measuring the overall GFP fluorescence, the cells were treated with 0.5M DTT (Sigma Aldrich, St Louis, Mo., USA) for 60 minutes to selectively remove surface-displayed (external) GFP and the GFP fluorescence measured again using a flow cytometer to quantify the fluorescence contribution derived from surface-displayed GFP.

To create the dual random loop libraries, the scaffold including the added restriction sites was left unaltered while the 9 amino acids inserted at Asp 102-Asp 103 and the 8 amino acids inserted at Glu172-Asp173 were simultaneously randomized (see FIG. 6 for schematic, and Table 7 for primers used). Briefly, starting with a selected scaffold, primers encoding for NNK sequences (Korndorfer I P et al., Journal of Molecular Biology, 330:385-396, 2003) were used to create regions I and III having randomized DNA sequences in place of the CDR sequences. The regions of I and III homologous to the central region II were extended and assembly PCR was utilized to create a single assembled fragment which was further amplified. Homologous recombination was used to create the resultant dual loop-inserted libraries. For the creation of the 37-2-7 dual loop library where the randomized loops contained only tyrosine and serine residues (Schlehuber S et al., Journal of Molecular Biology, 297:1105-1120, 2000), the above procedure was followed with primers instead containing TMY repeat sequence.

Library Screening and Selection

For scaffold evolution, all libraries were grown in selective SD-CAA medium at 30° C. to an OD$_{600}$ of 1.0 and were induced at 20° C. or 37° C. in SG-CAA for 12-16 hours. For 70° C. selections, induced yeast were first subject to thermal denaturation for 30 minutes prior to sorting. The yeast display libraries were labeled with anti-c-myc antibody (1:100 dilution) (Covance, Calif., USA) followed by anti-mouse phycoerythrin (PE) (1:40 dilution) (Sigma Aldrich, St Louis, Mo., USA). The library was first enriched for GFP positive clones for two to three rounds of sorting and the last round involved a stringent gate selecting cells with both GFP fluorescence and the presence of the c-myc epitope tag. All sort experiments were performed on a Becton Dickinson FACSVantage SE flow cytometric sorter at the University of Wisconsin Comprehensive Cancer Center. The recovered clones were sequenced using the PNL6 primer (Feldhaus M J, *Nature Biotechnology*, 21:163-170, 2003) (University of Wisconsin Biotechnology Center).

For selection of GFAbs, the dual random loop libraries using scaffolds 37-2-7, 70C-3, 20-4-8, and 20-5-8 were pooled together, induced, and labeled with anti c-myc antibody (Covance, Calif., USA) followed by anti mouse PE (Sigma Aldrich, St. Louis, Mo., USA). The double GFP and PE positive pool was collected and this pooled library was the source library for all binding selections. The intrinsic fluorescence of streptavidin PE and biotinylated PE was used for recovery of GFAbs against these ligands, whereas tyrosine kinase receptor B (TrkB) (R & D Systems, Minneapolis, Minn., USA) and glyceraldehyde-3-phosphate dehydrogenase (GAPDH) (Sigma Aldrich, St. Louis, Mo., USA) were first biotinylated for detection of ligand binding. All of the binders isolated were tested for affinity to secondary reagents and no cross-reactivity to an irrelevant biotinylated ligand (500 nM hen egg lysozyme) was detected. Any detected binding to secondary reagents is noted in Table 6. Details are disclosed below.

For isolation of streptavidin PE binders, the GFAb library was incubated with streptavidin PE at a concentration of 9.4 nM. To isolate phycoerythrin binders, we treated the GFAb library with biotinylated PE (Invitrogen, Carlsbad, Calif., USA) at a concentration of 1 µM. Recombinant monomeric human tyrosine kinase receptor B (TrkB) (R & D Systems, Minneapolis, Minn., USA) and glyceraldehyde-3-phosphate dehydrogenase (GAPDH) from human erythrocytes (Sigma Aldrich, St. Louis, Mo., USA) were biotinylated using Sulfo-NHS-LC-biotin (Pierce, Rockford, Ill., USA). The GFAb library pool was incubated with biotinylated TrkB at a concentration of 250 nM. The same procedure was followed to isolate GFP-based binders against biotinylated GAPDH which was utilized at a concentration of 500 nM. Secondary fluorophores were alternated between streptavidin PE, anti-biotin (Neomarkers, Fremont, Calif., USA) followed by anti-mouse PE, and anti-biotin followed by anti-mouse Alexa 647 (Invitrogen, Carlsbad, Calif., USA) to lessen the likelihood of recovering binders against the secondary reagents. The potential for such secondary binders is present in all naïve libraries, and as indicated by our pilot streptavidin PE and biotinylated PE selections these also exist in the GFAb library. Any such instances of secondary reagent binding are indicated in Table 6. The biotinylation of GAPDH and TrkB did not effect GFAb binding as binding could be detected with the unmodified antigen using anti-GAPDH (Chemicon, Millipore, Billerica, Mass., USA) and anti-TrkB (R & D Systems, Minneapolis, Minn., USA) antibodies for detection on the surface of yeast. Recombinant human TrkB/Fc chimera (R & D Systems, Minneapolis, Minn., USA), recombinant human TrkA/Fc (R & D Systems, Minneapolis, Minn., USA), and recombinant human TrkC/Fc (R & D Systems, Minneapolis, Minn., USA) were used to test T3 specificity.

Protein Secretion and Purification

Scaffold and GFAb open reading frames were subcloned from the pCT-ESO display construct to the pRS316-GFP expression vector by NhEI-BamHI digest (Huang D & Shusta E V, *Biotechnology Progress*, 21:349-357, 2005). BJ5464 transformed cells were grown for 72 hours in SD-CAA at 30° C. The media was switched to SG-CAA supplemented with BSA for 72 hours at 20° C. Protein purification was performed using a Ni-NTA column (Qiagen, Valencia, Calif., USA) as described earlier (Huang D & Shusta E V, *Biotechnology Progress*, 21:349-357, 2005). Relative secretion levels were determined by Western blotting using the anti-c-myc antibody as described earlier (Huang D & Shusta E V, *Biotechnology Progress*, 21:349-357, 2005). Fluorescence properties of the purified protein as reported in Table 4, were measured as described above.

Characterization of GFAbs

Binding affinity was determined using yeast surface display (Chao G et al., *Nat Protoc*, 1:755-768, 2006). Yeast displaying GFAbs were incubated with different concentrations of ligand for one hour on ice. Binding was subsequently detected using the secondary reagent combinations detailed above and quantified by flow cytometry. The dissociation constant was obtained by fitting the binding curve to a two parameter equilibrium binding model as previously described (Chao G et al., *Nat Protoc*, 1:755-768, 2006). To determine if both loops contributed to binding, unique restriction sites upstream and downstream of the ORF were used to singly re-insert the surrogate loop into position 102-103 or 172-173. The effect of loops on affinity of TrkB binder T3 and GAPDH binder G6 were measured using yeast surface display. For details regarding the measurement of soluble GFAb properties in FIG. 3, please see above for details.

Measurement of Soluble Protein Fluorescence Properties

Purified GFPM and 37-2-7 were diluted to prepare five samples with $OD_{488}$ 0.1 and lower. The emission spectrum for each dilution was measured (488 nm excitation) and the area under the curve computed. A plot of area under the curve for various dilutions was plotted for the samples. Sodium fluorescein (Sigma Aldrich, St. Louis, Mo., USA) was diluted in 0.1M NaOH and utilized as a standard with a quantum yield of 0.92. A similar trace of area under the curve versus dilutions used was prepared to compute the quantum efficiencies of GFPM and clone 37-2-7. All measurements were performed on a Jovan Yvon Horiba FluoroMax-3. To measure the extinction coefficient at 488 nm, the protein sample concentration was measured using the BCA kit (Pierce, Rockford, Ill., USA). The optical density was measured and divided by the concentration of the protein sample to obtain the extinction coefficient. For all other scaffolds and GFAbs, single dilution extinction coefficient and quantum yield measurements were performed using the same procedure as above except relative protein concentration measurements were made by Western blotting.

Measurement of Soluble GFAb Binding Properties

HEK 293 T/17 cells (human embryonic kidney cell line) were cultured using DMEM media (Gibco, Invitrogen, Carlsbad, Calif., USA) in 24 well plates. The cells were washed twice using PBS supplemented with BSA at 10 mg/ml. They were fixed for five minutes using a 1:1 mixture of methanol and acetone. The cells were washed twice with PBS-BSA and incubated for 90 minutes with 150 µl of GAPDH binder G6 or an equal concentration of the scaffold 20-5-8 as a negative control. The cells were subsequently washed twice and fixed using 4% para-formaldehyde for four minutes. The cells were imaged using an Olympus IX70 fluorescence microscope with an excitation wavelength of 445±20 nm and an emission wavelength of 509±24 nm. As a positive control, HEK cells were labeled with anti-GAPDH monoclonal antibody (1:100) (Chemicon, Millipore, Billerica, Mass., USA) for one hour followed by anti-mouse Alexa 488 (Molecular Probes, Invitrogen, Carlsbad, Calif., USA) for 30 minutes. DAPI was utilized as a nuclear stain.

For the Streptavidin-PE binder, 1.3 GFAb, which binds to streptavidin alone, 5 μl of streptavidin-coated polystyrene beads (Spherotech, Lake Forest, Ill., USA) with a mean particle diameter of 3.2 μm were washed with PBS-BSA (1 g/L). The beads were incubated with PBS-BSA for 20 minutes followed by incubation with 500 nM of 1.3 GFAb. An equal concentration of scaffold 20-5-8 was utilized as a control, and 400 nM streptavidin-PE was used in some samples as a competitive inhibitor. After one hour, the beads were washed with PBS-BSA and viewed on an Olympus IX70 fluorescence microscope and analyzed by flow cytometry.

Measurement of soluble T3 GFAb affinity was performed using antigen-loaded beads combined with flow cytometry. Briefly, streptavidin-coated polystyrene beads were washed in PBS-BSA (1 g/L). The beads were coated with biotinylated monomeric TrkB (approx 0.45 mg/ml) for 1 hour at room temperature on a rocker. The beads were blocked with of PBS-BSA (10 g/L) for 1 hour at room temperature. The TrkB-loaded beads were then incubated with serial dilutions of GFAb T3 always kept in molar excess by using increasing volumes (Vogt M & Skerra A, *Chembiochem* 5:191-199, 2004) for 1 hour with rocking. The beads were washed in PBS-BSA (1 g/L) and GFP fluorescence quantified by flow cytometry. The equilibrium dissociation constant was then determined by fitting the binding curve to a two parameter equilibrium binding model as described previously (Vogt M & Skerra A, *Chembiochem* 5:191-199, 2004). Soluble T3 GFAb affinity was also estimated by competition assay. Briefly, soluble T3 GFAb was incubated with soluble TrkB at known concentrations. Yeast displaying T3 GFAb were then used to measure the unbound concentration of TrkB in the solution phase binding mixture by FACS. Using equilibrium binding models representing both the solution phase interaction and the yeast surface interaction, the solution phase affinities were measured to be ~10 nM.

We claim:

1. A mutated fluorescent protein of either green fluorescent protein (GFP) or green fluorescent protein variants, wherein the mutated fluorescent protein comprises GFP mutations D19N, F64L and A87T, wherein the mutated fluorescent protein fluoresces when a heterologous amino acid sequence SEQ ID NO. 26 is inserted at insertion sites between Glu172-Asp173 and a heterologous amino acid sequence SEQ ID NO. 25 is inserted at insertion sites between Asp102-Asp103.

2. The mutated fluorescent protein of claim 1, wherein the mutated fluorescent protein is GFP comprising the mutations D19N, F64L and A87T.

3. The mutated fluorescent protein of claim 1, wherein the mutated fluorescent protein further comprises a GFP mutation V163A.

4. The mutated fluorescent protein of claim 3, wherein the mutated fluorescent protein further comprises GFP mutations Y39H, N105T, D117G, E172K and L221V.

5. The mutated fluorescent protein of claim 4, wherein the mutated fluorescent protein further comprises a GFP mutation F223S.

6. The mutated fluorescent protein of claim 1, wherein the mutated fluorescent protein further comprises:
 (a) a first amino acid sequence comprising at least one restriction site capable of being recognized by restriction enzymes inserted at a first insertion site between the amino acids Glu172 and Asp173 of GFP, and
 (b) a second amino acid sequence comprising at least one restriction site capable of being recognized by restriction enzymes inserted at a second insertion site between the amino acids Asp102 and Asp103 of GFP.

7. The mutated fluorescent protein of claim 6, wherein the first and second amino acid sequences each comprise at least two restriction sites that are not identical.

* * * * *

SEQUENCE LISTING

```
<160> NUMBER OF SEQ ID NOS: 64

<210> SEQ ID NO 1
<211> LENGTH: 714
<212> TYPE: DNA
<213> ORGANISM: Artificial Sequence
<220> FEATURE:
<223> OTHER INFORMATION: DNA sequence encoding yEGFP

<400> SEQUENCE: 1
atgtctaaag gtgaagaatt attcactggt gttgtcccaa ttttggttga attagatggt      60
gatgttaatg gtcacaaatt ttctgtctcc ggtgaaggtg aaggtgatgc tacttacggt     120
aaattgacct taaaattat ttgtactact ggtaaattgc cagttccatg gccaacctta     180
gtcactactt tcggttatgg tgttcaatgt tttgcgagat acccagatca tatgaaacaa     240
catgactttt tcaagtctgc catgccagaa ggttatgttc aagaaagaac tatttttttc     300
aaagatgacg gtaactacaa gaccagagct gaagtcaagt ttgaaggtga tacccttagtt    360 aatagaatcg aattaaaagg tattgatttt aaagaagatg gtaacatttt aggtcacaaa    420
ttggaataca actataactc tcacaatgtt tacatcatgg ctgacaaaca aaagaatggt    480
atcaaagtta acttcaaaat tagacacaac attgaagatg gttctgttca attagctgac    540
cattatcaac aaaatactcc aattggtgat ggtccagtct tgttaccaga caaccattac    600
ttatccactc aatctgcctt atccaaagat ccaaacgaaa agagagacca catggtcttg    660
ttagaatttg ttactgctgc tggtattacc catggtatgg atgaattgta caaa          714

<210> SEQ ID NO 2
<211> LENGTH: 239
<212> TYPE: PRT
<213> ORGANISM: Artificial Sequence
<220> FEATURE:
<223> OTHER INFORMATION: Amino acid sequence of yEGFP

<400> SEQUENCE: 2

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30
```

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
 50                  55                  60

Gly Tyr Gly Val Gln Cys Phe Ala Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Gly
225                 230                 235

<210> SEQ ID NO 3
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 3
cttatccact caatctaagt tatccaaaga tccaaac                                37

<210> SEQ ID NO 4
<211> LENGTH: 37
<212> TYPE: DNA
<213> ORGANISM: Artificial Sequence
<220> FEATURE:
<223> OTHER INFORMATION: Synthetic oligonuleotide

<400> SEQUENCE: 4
gtttggatct tggataact tagattgagt ggataag                                37

<210> SEQ ID NO 5
<211> LENGTH: 44
<212> TYPE: DNA
<213> ORGANISM: Artificial Sequence
<220> FEATURE:
<223> OTHER INFORMATION: Synthetic oligonuleotide

<400> SEQUENCE: 5
gaactatttt tttcaaagat cttaagacta gtgacggtaa ctac                        44

<210> SEQ ID NO 6
<211> LENGTH: 44
<212> TYPE: DNA

```
<213> ORGANISM: Artificial Sequence
<220> FEATURE:
<223> OTHER INFORMATION: Synthetic oligonuleotide

<400> SEQUENCE: 6
ctggtcttgt agttaccgtc actagtctta agatctttga aaaa                    44

<210> SEQ ID NO 7
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 7
caaaattaga cacaacattg aatctagaac gcgtgatggt tct                     43

<210> SEQ ID NO 8
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 8
gctaattgaa cagaaccatc acgcgttcta gattcaatgt tgt                     43

<210> SEQ ID NO 9
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 9
gtggaggagg ctctggtgga ggcggtagcg gaggcggagg gtcggctagc              50

<210> SEQ ID NO 10
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 10
gaacaaaagc ttatttctga agaggacttg taatagctga gatctgata               49

<210> SEQ ID NO 11
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 11
ttaagcaaca tttttggagt actcctcgga cga                                33

<210> SEQ ID NO 12
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 12
ctagtcgtcc gaggagtact ccaaaaatgt tgc                                33
```

```
<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 13
ctagagagag agattatagg cttgactaca                                       30

<210> SEQ ID NO 14
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 14
cgcgtgtagt caagcctata atctctctct                                       30

<210> SEQ ID NO 15
<211> LENGTH: 69
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (22)..(48)
<223> OTHER INFORMATION: nucleotides 22-48 can be any nucleotides that
      do not encode stop codon

<400> SEQUENCE: 15
cttgtagtta ccgtcactag tnnnnnnnnn nnnnnnnnnn nnnnnnnnct taagatcttt      60
gaaaaaaat                                                              69

<210> SEQ ID NO 16
<211> LENGTH: 66
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (22)..(45)
<223> OTHER INFORMATION: nucleotides 22 to 45 can be any nucleotides
      that do not encode stop codon

<400> SEQUENCE: 16
agacacaaca ttgaatctag annnnnnnnn nnnnnnnnnn nnnnacgcg tgatggttct       60 gttcaa                                                                 66

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
actagtgacg gtaactacaa g                                                21

<210> SEQ ID NO 18
<211> LENGTH: 21
<212> TYPE: DNA
<213> ORGANISM: Artificial Sequence
<220> FEATURE:
```

```
<223> OTHER INFORMATION: Synthetic oligonucleotide

<400> SEQUENCE: 18
tctagattca atgttgtgtc t                                              21

<210> SEQ ID NO 19
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 19
aaacttgact tcagctctgg tcttgtagtt accgtcacta gt                       42

<210> SEQ ID NO 20
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 20
aatggtatca aagctaactt caaaattaga cacaacattg aatctaga                 48

<210> SEQ ID NO 21
<211> LENGTH: 4
<212> TYPE: PRT
<213> ORGANISM: Artificial Sequence
<220> FEATURE:
<223> OTHER INFORMATION: Amino acids inserted between Asp102 and Asp103
      in the plasmid GFPM-AS

<400> SEQUENCE: 21

Leu Lys Thr Ser
1

<210> SEQ ID NO 22
<211> LENGTH: 4
<212> TYPE: PRT
<213> ORGANISM: Artificial Sequence
<220> FEATURE:
<223> OTHER INFORMATION: Amino acids inserted between Glu172 and Asp173
      in the plasmid GFPM-XM

<400> SEQUENCE: 22

Ser Arg Thr Arg
1

<210> SEQ ID NO 23
<211> LENGTH: 4
<212> TYPE: PRT
<213> ORGANISM: Artificial Sequence
<220> FEATURE:
<223> OTHER INFORMATION: Amino acids inserted between Asp102 and Asp103
      in the plasmid GFPM-ASXM

<400> SEQUENCE: 23

Leu Lys Thr Ser
1

<210> SEQ ID NO 24
<211> LENGTH: 4
<212> TYPE: PRT
<213> ORGANISM: Artificial Sequence
<220> FEATURE:
<223> OTHER INFORMATION: Amino acids inserted between Glu172 and Asp173
      in the plasmid GFPM-ASXM
```

<400> SEQUENCE: 24

Ser Arg Thr Arg
1

<210> SEQ ID NO 25
<211> LENGTH: 13
<212> TYPE: PRT
<213> ORGANISM: Artificial Sequence
<220> FEATURE:
<223> OTHER INFORMATION: Amino acids inserted between Asp102 and Asp103
      in the plasmid GFPM-ASL3

<400> SEQUENCE: 25

Leu Lys Gln His Phe Trp Ser Thr Pro Arg Thr Thr Ser
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Amino acids inserted between Glu172-Asp173 in
      the plasmid GFPM-XMH3

<400> SEQUENCE: 26

Ser Arg Glu Arg Asp Tyr Arg Leu Asp Tyr Thr Arg
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Amino acids inserted between Asp102 and Asp103
      in the plasmid GFP-H3L3

<400> SEQUENCE: 27

Leu Lys Gln His Phe Trp Ser Thr Pro Arg Thr Thr Ser
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Amino acids inserted between Glu172 and Asp173
      in the plasmid GFP-H3L3

<400> SEQUENCE: 28

Ser Arg Glu Arg Asp Tyr Arg Leu Asp Tyr Thr Arg
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone T1

<400> SEQUENCE: 29

Ser Lys Ser Arg Ser Leu Glu Ser Val
1               5

<210> SEQ ID NO 30
<211> LENGTH: 8
<212> TYPE: PRT

```
<213> ORGANISM: Artificial Sequence
<220> FEATURE:
<223> OTHER INFORMATION: Amino acids inserted between Glu172 and Asp173
      in clone T1

<400> SEQUENCE: 30

Gly Tyr Leu Arg Trp Leu Phe Gly
1               5

<210> SEQ ID NO 31
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone T2

<400> SEQUENCE: 31

Val Ile Asn Pro Phe Thr Val Arg Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone T2

<400> SEQUENCE: 32

Asn Ala Trp Val Val His Arg Arg
1               5

<210> SEQ ID NO 33
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone T3

<400> SEQUENCE: 33

Pro Ser Trp Trp Ser Leu Phe Phe Pro
1               5

<210> SEQ ID NO 34
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone T3

<400> SEQUENCE: 34

Ser Thr Ala Thr Gly Leu Phe Ala
1               5

<210> SEQ ID NO 35
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone G6

<400> SEQUENCE: 35

Arg Val Ser Arg Phe Leu Leu Thr Thr
1               5
```

-continued

<210> SEQ ID NO 36
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone G6

<400> SEQUENCE: 36

Lys Ser Arg Ile Ile Ser Ser Gln
1               5

<210> SEQ ID NO 37
<211> LENGTH: 9
<212> TYPE: PRT
<213> ORGANISM: Artificial Sequence
<220> FEATURE:
<223> OTHER INFORMATION: Amino acids inserted between Asp172 and Asp173
      in clone G7

<400> SEQUENCE: 37

Asn Val Ile Tyr Pro Phe Leu Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone G7

<400> SEQUENCE: 38

Arg Val Thr Lys Thr Lys His Lys
1               5

<210> SEQ ID NO 39
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone G4

<400> SEQUENCE: 39

Arg Gly Val Ser Lys Ser Phe Leu Leu
1               5

<210> SEQ ID NO 40
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone G4

<400> SEQUENCE: 40

Gln Gly Ile Thr Lys Gly Tyr Lys
1               5

<210> SEQ ID NO 41
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone G8

<400> SEQUENCE: 41

```
Ser His Cys Leu Phe Arg Lys Cys Tyr
1               5
```

<210> SEQ ID NO 42
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone G8

<400> SEQUENCE: 42

```
Ala Arg Ser Ile Arg Met Lys Val
1               5
```

<210> SEQ ID NO 43
<211> LENGTH: 9
<212> TYPE: PRT
<213> ORGANISM: Artificial Sequence
<220> FEATURE:
<223> OTHER INFORMATION: Amino acids inserted between Asp102 and Asp102
      in clone 1.3

<400> SEQUENCE: 43

```
Ala Ile Ser Arg Ser Phe Phe Ser Thr
1               5
```

<210> SEQ ID NO 44
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone 1.3

<400> SEQUENCE: 44

```
Ile Arg Asn Leu Lys Tyr Thr Asn
1               5
```

<210> SEQ ID NO 45
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone 2.7

<400> SEQUENCE: 45

```
Val Phe Ser Ser Leu Arg Tyr His Val
1               5
```

<210> SEQ ID NO 46
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone 2.7

<400> SEQUENCE: 46

```
Leu Arg Met Asp Asp Thr Asn Pro
1               5
```

<210> SEQ ID NO 47
<211> LENGTH: 9
<212> TYPE: PRT
<213> ORGANISM: Artificial Sequence
<220> FEATURE:

<223> OTHER INFORMATION: Amino acids inserted between Asp102 and Asp102
      in clone 2.17

<400> SEQUENCE: 47

Lys Ala Arg Met Arg Leu Phe Leu Met
1               5

<210> SEQ ID NO 48
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone 2.17

<400> SEQUENCE: 48

Glu Tyr Gly Asp Thr Leu Leu Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone 2

<400> SEQUENCE: 49

Arg Gly Leu Phe Trp Pro Val Leu Ile
1               5

<210> SEQ ID NO 50
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone 2

<400> SEQUENCE: 50

Pro Asn Pro Val Phe Arg Gln Asn
1               5

<210> SEQ ID NO 51
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone 5

<400> SEQUENCE: 51

Ser Cys Ser Trp Cys Leu Phe Thr Leu
1               5

<210> SEQ ID NO 52
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone 5

<400> SEQUENCE: 52

Lys Asn Gln Met Gly Met Gly Lys
1               5

<210> SEQ ID NO 53

```
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone 12

<400> SEQUENCE: 53

Lys Ser His Phe Thr Ile Phe Arg Thr
1               5

<210> SEQ ID NO 54
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone 12

<400> SEQUENCE: 54

Asp Gly Trp Arg Arg Thr Thr Val
1               5

<210> SEQ ID NO 55
<211> LENGTH: 9
<212> TYPE: PRT
<213> ORGANISM: Artificial Sequence
<220> FEATURE:
<223> OTHER INFORMATION: Amino acids inserted between Asp102 and Asp103
      in clone 16

<400> SEQUENCE: 55

Asn Cys Arg Trp Cys Thr Tyr Tyr Leu
1               5

<210> SEQ ID NO 56
<211> LENGTH: 8
<212> TYPE: PRT
<213> ORGANISM: Artificial Sequence
<220> FEATURE:
<223> OTHER INFORMATION: Amino acids inserted between Glu172 and Asp173
      in clone 16

<400> SEQUENCE: 56

Ser Thr Ser Asn Trp Met Arg Met
1               5

<210> SEQ ID NO 57
<211> LENGTH: 225
<212> TYPE: PRT
<213> ORGANISM: Unknown
<220> FEATURE:
<223> OTHER INFORMATION: Discosoma sp. red fluoresecnt protein

<400> SEQUENCE: 57

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
                20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
        50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
```

```
                        85                  90                  95
Met Asn Phe Glu Asp Gly Gly Val Val Thr Val Thr Gln Asp Ser Ser
                    100                 105                 110

Leu Gln Asp Gly Cys Phe Ile Tyr Lys Val Lys Phe Ile Gly Val Asn
                115                 120                 125

Phe Pro Ser Asp Gly Pro Val Met Gln Lys Lys Thr Met Gly Trp Glu
            130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 58
<211> LENGTH: 225
<212> TYPE: PRT
<213> ORGANISM: Artificial Sequence
<220> FEATURE:
<223> OTHER INFORMATION: Improved monomeric red fluorescent protein

<400> SEQUENCE: 58

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
                20                  25                  30

Gly Glu Gly Arg Pro Tyr Glu Gly Thr Gln Thr Ala Lys Leu Lys Val
            35                  40                  45

Thr Lys Gly Gly Pro Leu Pro Phe Ala Trp Asp Ile Leu Ser Pro Gln
        50                  55                  60

Phe Gln Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220
```

Ala
225

<210> SEQ ID NO 59
<211> LENGTH: 236
<212> TYPE: PRT
<213> ORGANISM: Artificial Sequence
<220> FEATURE:
<223> OTHER INFORMATION: Monomeric cherry fluorescent protein

<400> SEQUENCE: 59

```
Met Val Ser Lys Gly Glu Glu Asp Asn Met Ala Ile Ile Lys Glu Phe
1               5                  10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

<210> SEQ ID NO 60
<211> LENGTH: 236
<212> TYPE: PRT
<213> ORGANISM: Artificial Sequence
<220> FEATURE:
<223> OTHER INFORMATION: Monomeric strawberry fluorescent protein

<400> SEQUENCE: 60

```
Met Val Ser Lys Gly Glu Glu Asn Asn Met Ala Ile Ile Lys Glu Phe
1               5                  10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60
```

Ile Leu Thr Pro Asn Phe Thr Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Leu Tyr Glu Arg Ala Glu Gly
    210                 215                 220

Arg His Ser Thr Gly Gly Met Asp Glu Leu Tyr Lys
225                 230                 235

<210> SEQ ID NO 61
<211> LENGTH: 225
<212> TYPE: PRT
<213> ORGANISM: Artificial Sequence
<220> FEATURE:
<223> OTHER INFORMATION: Monomeric tangerine fluorescent protein

<400> SEQUENCE: 61

Met Ala Ser Ser Glu Asp Val Ile Lys Glu Phe Met Arg Phe Lys Val
1               5                   10                  15

His Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Cys Tyr Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Ser Glu Arg Met Tyr Pro Glu Asp Gly Ala Leu Lys Gly Glu
145                 150                 155                 160

Ile Lys Gln Arg Leu Lys Leu Lys Asp Gly Gly His Tyr Asp Ala Glu
                165                 170                 175

Val Lys Thr Thr Tyr Lys Ala Lys Lys Pro Val Gln Leu Pro Gly Ala
            180                 185                 190

```
Tyr Lys Thr Asp Ile Lys Leu Asp Ile Thr Ser His Asn Glu Asp Tyr
        195                 200                 205

Thr Ile Val Glu Leu Tyr Glu Arg Ala Glu Gly Arg His Ser Thr Gly
210                 215                 220

Ala
225

<210> SEQ ID NO 62
<211> LENGTH: 236
<212> TYPE: PRT
<213> ORGANISM: Artificial Sequence
<220> FEATURE:
<223> OTHER INFORMATION: Improved monomeric orange fluorescent protein

<400> SEQUENCE: 62

Met Val Ser Lys Gly Glu Glu Asn Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Phe Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Thr Tyr Gly Ser Lys Ala Tyr Val Lys His
65                  70                  75                  80

Pro Ala Asp Ile Pro Asp Tyr Phe Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Thr Ser Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 63
<211> LENGTH: 236
<212> TYPE: PRT
<213> ORGANISM: Artificial Sequence
<220> FEATURE:
<223> OTHER INFORMATION: Monomeric banana fluorescent protein

<400> SEQUENCE: 63

Met Val Ser Lys Gly Glu Glu Asn Asn Met Ala Val Ile Lys Glu Phe
1               5                   10                  15

Met Arg Phe Lys Val His Met Glu Gly Ser Val Asn Gly His Glu Phe
            20                  25                  30
```

Glu Ile Glu Gly Glu Gly Gly Arg Pro Tyr Glu Gly Thr Gln Thr
        35                  40                  45

Ala Lys Leu Lys Val Thr Lys Gly Gly Pro Leu Pro Phe Ala Trp Asp
 50                  55                  60

Ile Leu Ser Pro Gln Phe Cys Tyr Gly Ser Lys Ala Tyr Val Lys His
65                  70                  75                  80

Pro Thr Gly Ile Pro Asp Tyr Phe Lys Leu Ser Phe Pro Glu Gly Phe
                85                  90                  95

Lys Trp Glu Arg Val Met Asn Phe Glu Asp Gly Gly Val Val Thr Val
                100                 105                 110

Ala Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Ser Ala Glu Thr Lys Thr Thr Tyr Lys Ala Lys Lys Pro Val
            180                 185                 190

Gln Leu Pro Gly Ala Tyr Ile Ala Gly Glu Lys Ile Asp Ile Thr Ser
        195                 200                 205

His Asn Glu Asp Tyr Thr Ile Val Glu Leu Tyr Glu Arg Ala Glu Gly
    210                 215                 220

Arg His Ser Thr Gly Gly Met Asp Glu Leu Tyr Lys
225                 230                 235

<210> SEQ ID NO 64
<211> LENGTH: 225
<212> TYPE: PRT
<213> ORGANISM: Artificial Sequence
<220> FEATURE:
<223> OTHER INFORMATION: Monomeric honeydew fluorescent protein

<400> SEQUENCE: 64

Met Ala Ser Ser Glu Asp Val Ile Lys Glu Phe Met Arg Phe Lys Val
1               5                   10                  15

His Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
 50                  55                  60

Phe Met Trp Gly Ser Lys Ala Tyr Val Lys His Pro Ala Asp Ile Pro
65                  70                  75                  80

Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Ala
    130                 135                 140

Ala Thr Ser Glu Arg Met Tyr Pro Glu Asp Gly Ala Leu Lys Gly Glu
145                 150                 155                 160

Ile Lys Gln Arg Leu Lys Leu Lys Asp Gly Gly His Tyr Asp Ala Glu

-continued

```
              165                 170                 175
Val Lys Thr Thr Tyr Lys Ala Lys Lys Pro Val Gln Leu Pro Gly Ala
            180                 185                 190

Tyr Lys Ile Asp Gly Lys Leu Asp Ile Thr Ser His Asn Glu Asp Tyr
        195                 200                 205

Thr Ile Val Glu Gln Tyr Glu Arg Ala Glu Gly Arg His Ser Thr Gly
        210                 215                 220

Ala
225
```